(12) United States Patent
Sidebotham et al.

(10) Patent No.: US 10,932,911 B2
(45) Date of Patent: Mar. 2, 2021

(54) IMPLANT FOR OSTEOTOMY AND CANINE OSTEOTOMY METHOD

(71) Applicant: BioMedtrix, LLC, Whippany, NJ (US)

(72) Inventors: Christopher G. Sidebotham, Boonton, NJ (US); Gregory Thomas van der Meulen, Ketchum, ID (US)

(73) Assignee: BioMedtrix, LLC, Whippany, NJ (US)

( * ) Notice: Subject to any disclaimer, the term of this patent is extended or adjusted under 35 U.S.C. 154(b) by 83 days.

(21) Appl. No.: 16/289,532

(22) Filed: Feb. 28, 2019

(65) Prior Publication Data

US 2019/0269514 A1 Sep. 5, 2019

Related U.S. Application Data

(60) Provisional application No. 62/637,244, filed on Mar. 1, 2018.

(51) Int. Cl.
*A61F 2/28* (2006.01)
*A61B 17/80* (2006.01)
*A61F 2/30* (2006.01)

(52) U.S. Cl.
CPC ............ *A61F 2/28* (2013.01); *A61B 17/8095* (2013.01); *A61F 2002/2892* (2013.01); *A61F 2002/307* (2013.01); *A61F 2002/30062* (2013.01); *A61F 2002/3093* (2013.01); *A61F 2002/30266* (2013.01); *A61F 2002/30281* (2013.01); *A61F 2002/30736* (2013.01); *A61F 2310/00017* (2013.01); *A61F 2310/00023* (2013.01); *A61F 2310/00029* (2013.01); *A61F 2310/00131* (2013.01); *A61F 2310/00329* (2013.01); *A61F 2310/00359* (2013.01); *A61F 2310/00365* (2013.01)

(58) Field of Classification Search
CPC .. A61F 2002/30266; A61F 2002/30281; A61F 2002/2892; A61F 2002/307; A61F 2002/30736; A61B 17/8095
See application file for complete search history.

(56) References Cited

U.S. PATENT DOCUMENTS

2013/0056912 A1 3/2013 O'Neill et al.
2018/0325568 A1 11/2018 Wotton

OTHER PUBLICATIONS

Other PDF of Fusion Implants—Advanced Veterinary Devices "Fusion TTA" product website, accessed from https://www.fusionimplants.com/; 1 pp., archived May 15, 2015.
PDF of Fusion Implants—Advanced Veterinary Devices "Implants" product website, accessed from https://www.fusionimplants.com/product-category/fusion-tta/implants/; 1 pp., archived Dec. 22, 2015.
"OrthoFoam MMP Wedge for Canine Cruciate Disease" User Guide, Orthomed (UK) Ltd., 40 pp., Oct. 2014.

*Primary Examiner* — David H Willse
*Assistant Examiner* — Javier G Blanco
(74) *Attorney, Agent, or Firm* — Klarquist Sparkman, LLP

(57) ABSTRACT

An implantable orthopedic wedge can include a main body having a base portion and an apical portion, the apical portion including a first end. The main body can have a thickness that tapers along a perimeter of the main body from a first thickness at the base portion to a second thickness at the apical portion. The implantable orthopedic wedge can also include a fixation member coupled to the main body and configured to receive one or more anchoring elements to anchor the wedge to an implantation site.

10 Claims, 22 Drawing Sheets

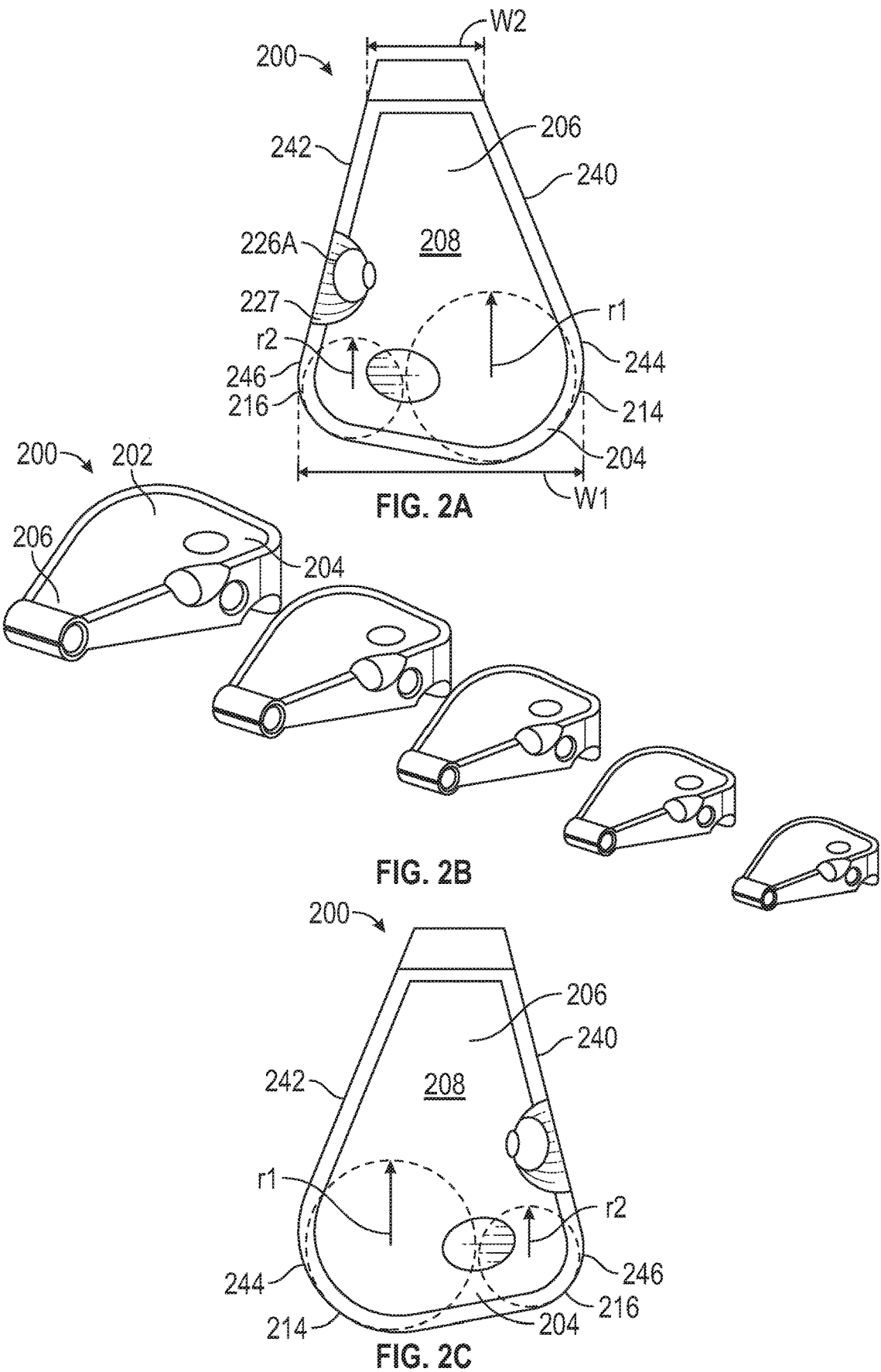

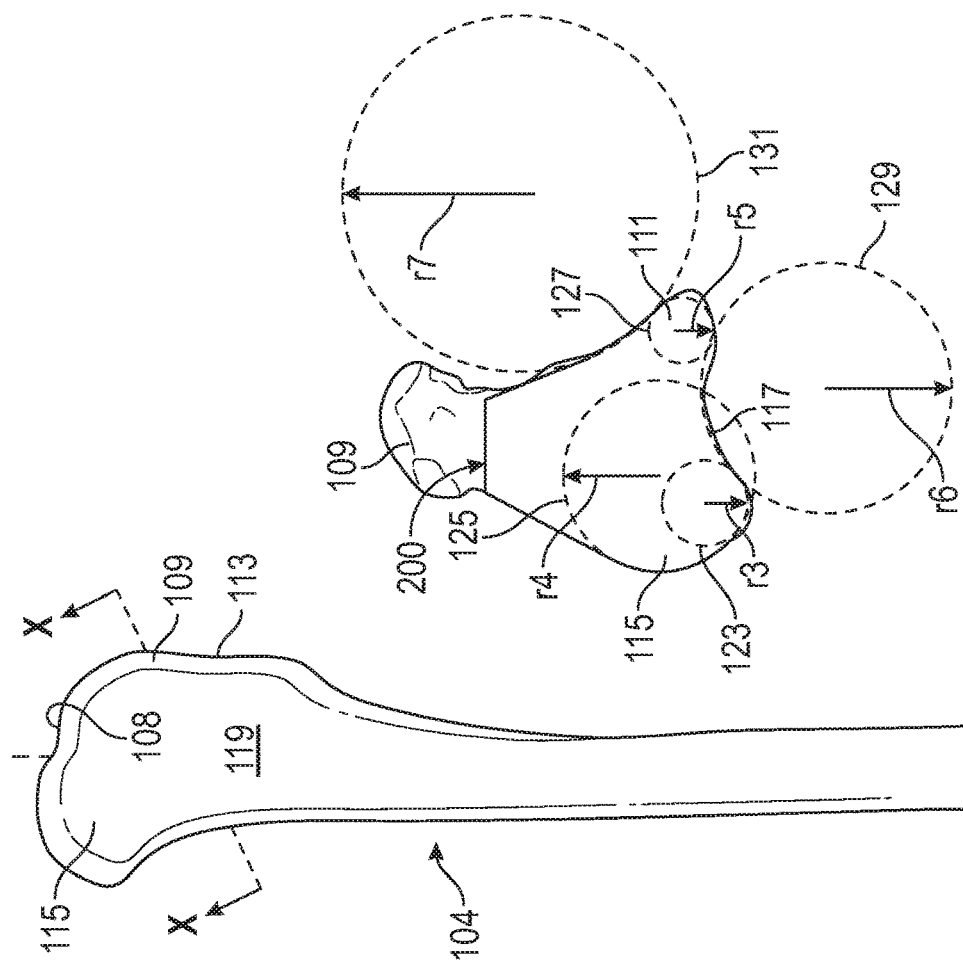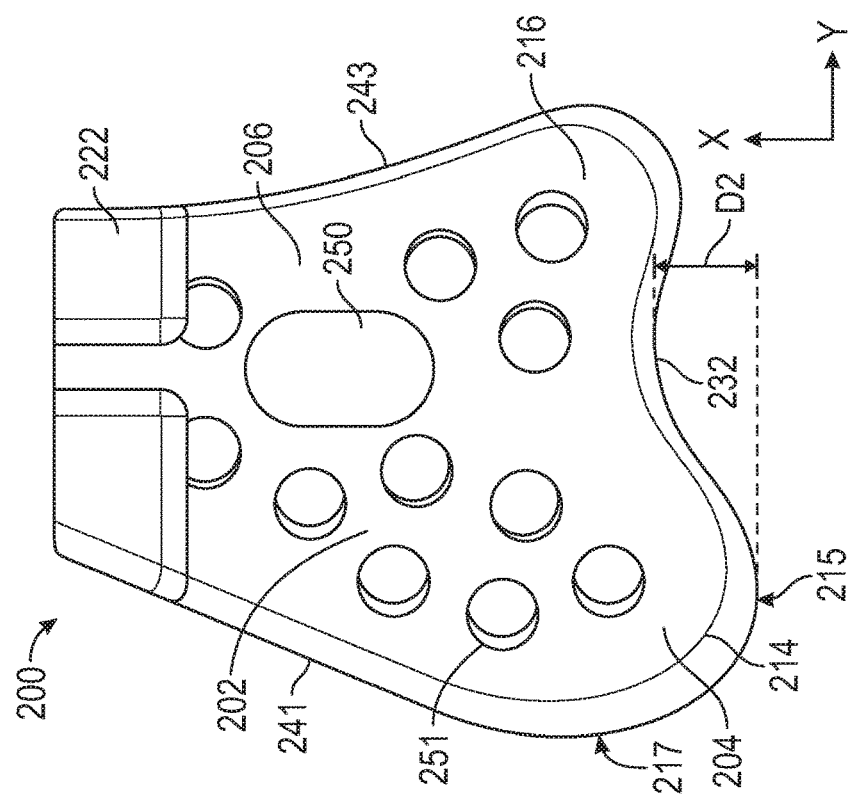

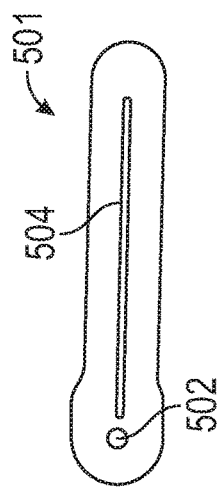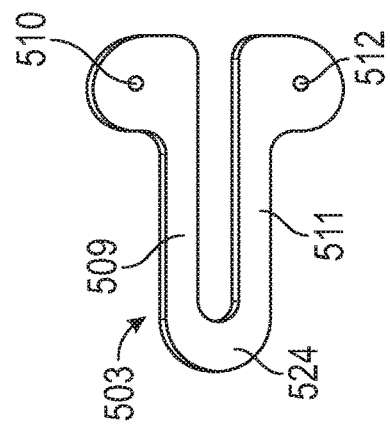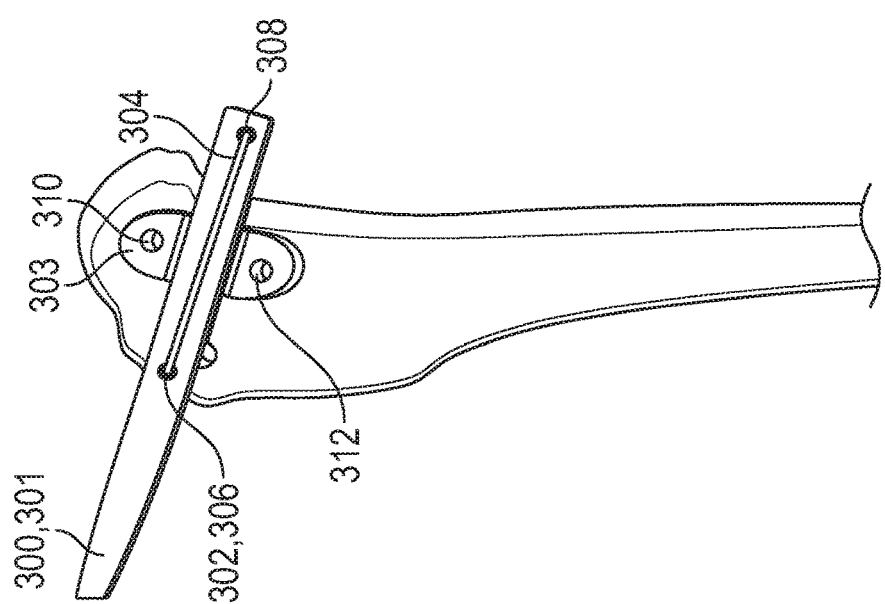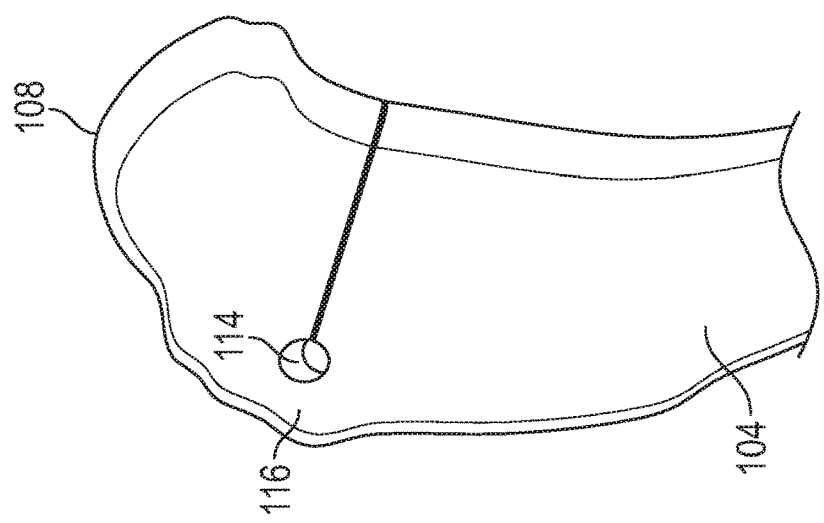

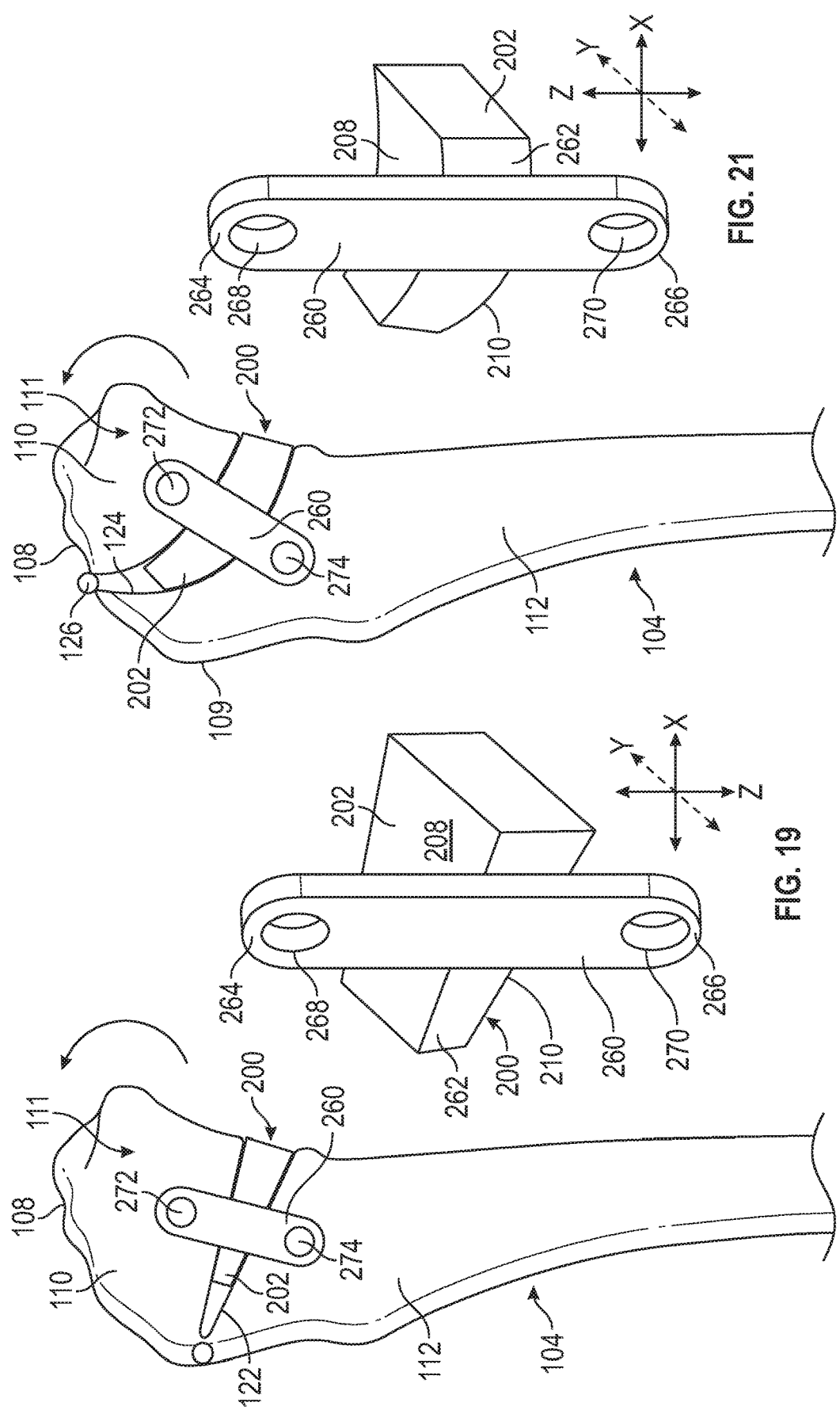

IMPLANT FOR OSTEOTOMY AND CANINE OSTEOTOMY METHOD

CROSS-REFERENCE TO RELATED APPLICATION

This application claims the benefit of U.S. Provisional Application No. 62/637,244, filed on Mar. 1, 2018, which is incorporated by reference herein in its entirety.

FIELD

This application pertains to implantable orthopedic devices for osteotomy procedures.

BACKGROUND

In veterinary orthopedics, rupture of the cranial cruciate ligament (CCL) in a dog's stifle (knee), is one of the most frequent orthopedic injuries. The result of this injury is instability of the knee with the tibia thrusting forward (cranially), causing discomfort and limiting mobility during normal daily activities (walking, running, etc.).

There are several surgical options to address this injury which include Tibial Plateau Leveling Osteotomy (TPLO), Tibial Tubercle Advancement (TTA), CORA-Based Leveling Osteotomy (CBLO) and Lateral Suture. The TPLO procedure remains the most popular clinically successful procedure based on re-establishing stability of the knee in the early post-operative period and achieving this with acceptable complications, but still up to 15% based on published articles.

The TTA procedure is an example of a straight cut osteotomy with an opening wedge application. The cut is made vertically (e.g., in a dorsal-ventral direction) caudal to the tibial tubercle. An orthopedic wedge is then inserted into the opening proximally, maintaining the advanced position of the tubercle. By advancing the tubercle, which is attached to the patellar ligament, the pull of the ligament becomes normal to the tibial plateau angle, eliminating the cranial thrust vector.

However, the TTA procedure does not consistently restore full stability to a knee after a torn CCL because stability in the TTA procedure relies solely on soft tissue, rather than on a combination of soft tissue and bone. There can also be complications in healing and function if the distal bridge of bone connecting the tubercle to the tibia fractures. In such cases, additional structure (e.g., a plate, cerclage wiring, and/or staples) can be applied to reinforce the area.

The TPLO procedure involves making a radial osteotomy through the medial side of the proximal tibia and then rotating that proximal segment of bone until the plateau of the tibia is more horizontal (e.g., originally 25° but changed to 6° through the TPLO technique). This rotation creates a mechanical stop prohibiting the tibia from advancing cranially relative to the femur, replacing the role of the CCL. With the proximal bone segment newly positioned, a bone plate and screws are used to bridge the osteotomy and hold that new position. A typical TPLO procedure can have a recovery period of 8-10 weeks, and is considered to be a technically demanding procedure.

The TPLO, TTA, CBLO, and lateral suture procedures can have varying levels of success and can involve complex surgical techniques that carry with them the risk of complications. Risks include extended healing time for the osteotomy, delayed restoration of function due to complications such as non-union of the osteotomy, and movement of the proximal segment of the tibia, all of which can require surgical intervention. In some cases, complications can require revision surgery to remove the implant and/or apply other techniques following the removal of the original implant. Furthermore, the radial cuts of the TPLO and CBLO procedures can be difficult to make accurately, and may potentially result in "rock back" of the tibial segment, which can destabilize the joint. Accordingly, there is a continuing need for improved surgical options to address rupture of the CCL.

SUMMARY

The present disclosure is directed toward new and non-obvious methods and apparatuses relating to surgical procedures for addressing rupture of the CCL. Described herein are embodiments of devices intended to be implanted in the knee region of a patient, as well as apparatuses and methods for implanting the same. The orthopedic devices can be used to help restore and/or replace the functionality of a defective knee. Such methods and apparatuses can improve upon existing techniques by simplifying the procedure, while still retaining both soft tissue and bone support to improve recovery.

An implantable orthopedic wedge can include a main body comprising a first end or base portion having a first thickness that tapers to a second end or apical portion having a second, smaller thickness, the base portion having a first width that tapers to a second, smaller width of the apical portion. The orthopedic wedge can be configured to be disposed within an osteotomy in a bone, such as the tibia. In some embodiments, the main body of the wedge can have a cross-section configured to align with a native cross section of the bone.

In some embodiments, the main body can comprise first and second concave surfaces. The edge portions of the concave surfaces can extend past the center portions, such that when the wedge is implanted within the knee region, the edge portions of the surfaces contact the outer cortex of the native bone.

In some embodiments, the implantable orthopedic wedge can comprise biocompatible materials such as titanium, stainless steel, cobalt chrome, tantalum, and/or bioresorbable materials such as PLLA (polylactic acid, polylactic acid with hydroxyapatite).

In some embodiments, the orthopedic wedge can further comprise a positioning member coupled to the apical portion of the main body. The positioning member can be configured to be disposed within a corresponding opening in the bone of a patient and can be configured to prevent movement of the orthopedic wedge within the patient after implantation.

In some embodiments, the orthopedic wedge can comprise a plurality of openings extending through the main body. In some embodiments, one or more openings can be configured as anchor openings such that an anchoring element (e.g., a screw) can extend through the opening and into the surrounding bone, thus coupling the orthopedic wedge to the bone. In some embodiments, one or more openings can be configured as ossification openings configured to promote bone growth through the wedge. In some embodiments, the ossification openings can comprise biologics within them, for example, bioglass, bone morphogenetic protein (BMP), and/or sclerostin.

In some embodiments, the orthopedic wedge can further comprise a fixation member configured to receive an anchoring element to anchor the wedge to an implantation site. In some embodiments, the fixation member can have a first end portion and a second end portion each comprising a respective aperture, and each aperture can be configured to receive a respective anchoring element.

In some embodiments, the main body of the orthopedic wedge can be curved with respect to a plane extending parallel to the width of the main body.

In a representative embodiment, an implantable orthopedic wedge comprises a main body and a fixation member. The main body having a base and an apical portion, the base having a first thickness that tapers to a second thickness of the apical portion, the second thickness being smaller than the first thickness. The base having a first width that tapers to a second width of the apical portion, the second width being smaller than the first width. The fixation member can be coupled to the main body and configured to receive one or more anchoring elements to anchor the wedge to an implantation site.

In some embodiments, the fixation member can be coupled to a side portion of the main body and can extend parallel to the thickness of the main body. In some embodiments, the fixation member has a first end portion and a second end portion each comprising a respective aperture, and each aperture can be configured to receive a respective anchoring element of the one or more anchoring elements. In some embodiments, the main body can comprise a central slot extending through the thickness of the main body, and the central slot can be configured to allow the one or more anchoring elements to extend through the central slot.

In some embodiments, the orthopedic wedge described above can be implanted using a method comprising drilling an opening in the native bone, performing a straight cut osteotomy, expanding the osteotomy and inserting the orthopedic wedge, and anchoring the orthopedic wedge to the surrounding bone using an anchoring element. Implantation of the orthopedic wedge can correct the slope of the native tibial plateau, thus providing biomechanical advantages without the trauma of the more complicated prior art surgical procedures. The orthopedic wedge can provide additional stability by allowing more normalized loading of the wedge and thereby mitigating complications with post-operative fusion of the osteotomy.

In a representative embodiment, the method of implanting the orthopedic wedge can comprise drilling an opening in the tubercle of a patient's tibia, cutting an osteotomy in a cranial-caudal direction through the tibia, connecting the osteotomy to the opening, expanding the osteotomy, disposing the orthopedic wedge within the osteotomy, releasing the osteotomy, and anchoring the orthopedic wedge to the surrounding bone.

In another representative embodiment, the method of implanting the orthopedic wedge can comprise drilling a tubercle opening in a medial-lateral direction through the tubercle of a patient's tibia, and aligning a saw guide with the tubercle opening such that a guide channel in the saw guide extends caudally from the opening. A saw is then aligned with the guide channel in the saw guide and the saw is used to cut along the guide channel, creating an osteotomy. In some embodiments, the osteotomy can be a curved osteotomy. The saw guide can then be removed and the saw can be used to connect the osteotomy to the tubercle opening. The osteotomy can then be expanded in a ventral-dorsal direction using an expander. Once expanded, the orthopedic wedge can be implanted within the osteotomy, with the positioning member of the orthopedic wedge being situated within the tubercle opening. The expander can then be released, allowing the osteotomy to contract such that the cortex of the native tibia abuts the orthopedic wedge.

In some embodiments, a second opening can be drilled through the native tibia and extending through the orthopedic wedge, and an anchoring element (e.g., a screw) can extend through the second opening, coupling the orthopedic wedge to the surrounding bone. The anchoring element can be used to compress the surrounding bone against the orthopedic wedge.

In other embodiments, the orthopedic wedge can further comprise a fixation member. One or more anchoring elements (e.g., screws) can extend through the fixation member, coupling the orthopedic wedge to the surrounding bone. In some embodiments, the orthopedic wedge can comprise a central slot extending through a width of the main body, and the anchoring elements can extend through the central slot.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosed technology will become more apparent from the following detailed description, which proceeds with reference to the accompanying figures.

BRIEF DESCRIPTION OF THE DRAWINGS

FIG. 2A illustrates an embodiment of an implantable orthopedic wedge configured for use in the tibia of the right hind limb of a dog.

FIG. 2B illustrates a perspective view of implantable orthopedic wedges of the type shown in FIG. 2A in various sizes.

FIG. 2C illustrates an embodiment of the implantable orthopedic wedge of FIG. 2A configured for use in the tibia of the left hind limb of a dog.

FIG. 6A illustrates a top plan view of another embodiment of an implantable orthopedic wedge configured for use in the tibia of the left hind limb of a dog.

FIG. 6B illustrates a medial side elevational view of a canine tibia.

FIG. 6C illustrates a cross-sectional view of the tibia of FIG. 6B taken along line X-X of FIG. 6B.

FIGS. 9-15 illustrate an exemplary method and devices for implanting an embodiment of an implantable orthopedic wedge.

FIG. 18 is a lateral view illustrating another embodiment of an orthopedic wedge implanted within a tibia and including a fixation member.

FIG. 19 illustrates a perspective view of the orthopedic wedge of FIG. 18.

FIG. 20 is a lateral view illustrating another embodiment of an orthopedic wedge including a curved main body and a fixation member implanted within a tibia.

FIG. 21 illustrates a perspective view of the orthopedic wedge of FIG. 20.

DETAILED DESCRIPTION

General Considerations

Figure 1A:
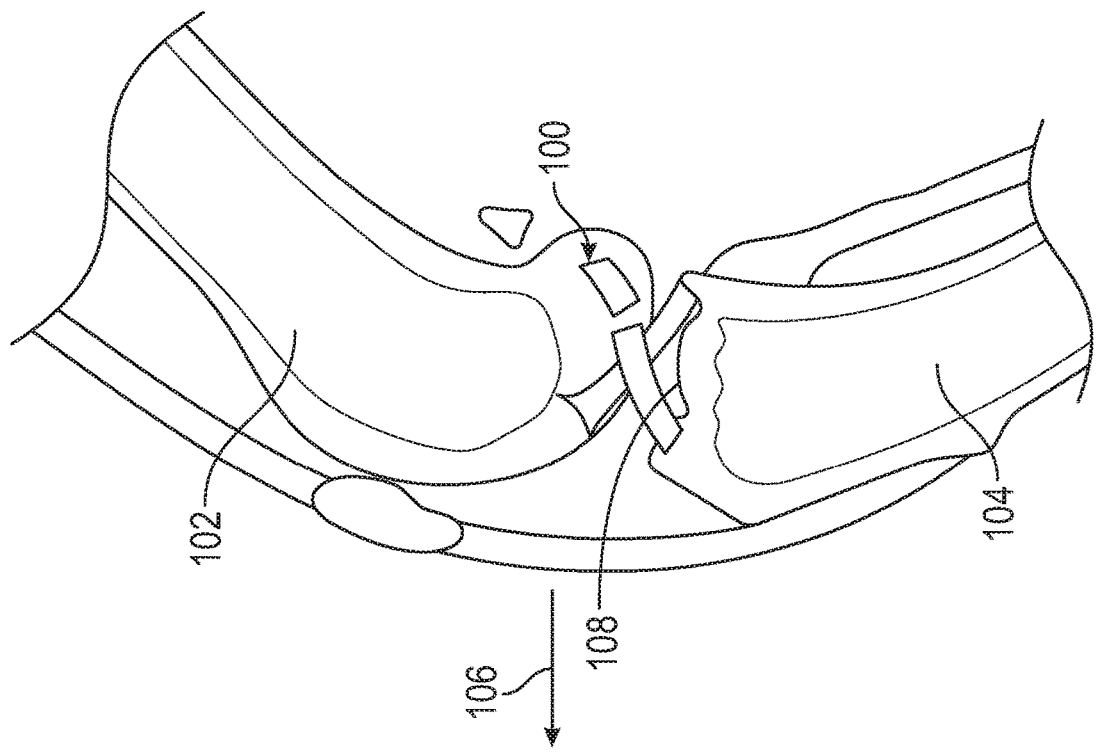
FIGS. 1A-1B are medial side elevation views of the canine knee illustrating an intact (1A) and ruptured (1B) cranial cruciate ligament.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "cranial" refers to a direction toward the head of the patient and the term "caudal" refers to a direction away from the head toward the tail of the patient. A "cranial view" of an object is a view from a perspective looking at the cranial surface or aspect of the object. A "caudal view" is a view from a perspective looking at the caudal surface or aspect of the object. The term "medial" refers to a direction toward the center of the patient's body mass and the term "lateral" refers to a direction away from the center of the patient's body mass. The term "dorsal" refers to a direction toward the patient's spine and the term "ventral" refers to a direction away from the patient's spine. For the purposes of this application, the apparatus and method are described using these terms in the context of a veterinary patient. It is understood that in the context of a human patient, the cranial/caudal and dorsal/ventral directions will differ.

As used herein, the term "proximal" refers to a direction toward the point of origin or attachment, frequently toward the user in the context of a surgical instrument. As used herein, the term "distal" refers to a direction away from the point of origin or attachment, frequently away from the user in the context of a surgical instrument. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing dimensions (e.g., heights, widths, lengths, etc.), angles, quantities of components, percentages, temperatures, forces, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

EXEMPLARY EMBODIMENTS

Disclosed herein are embodiments of implantable orthopedic devices that are primarily intended to be implanted in a canine knee, and methods for implanting the same. For example, the orthopedic devices described herein can be used to help restore and/or replace the functionality of a defective cranial cruciate ligament (CCL).

In human and animal orthopedics, straight osteotomies, radial osteotomies, and spherical osteotomies can be created at specific locations in long bones to achieve realignment of a bone segment to the overall limb axis for improved biomechanics and/or to help restore and/or replace the functionality of defective ligaments.

There are multiple physiological problems associated with long bones that can affect limb biomechanics, which can occur as a result of trauma (e.g., bone fractures that heal in a misaligned position), and/or birth defects. Surgical methods of re-establishing appropriate biomechanics of a limb can include repositioning proximal and distal bone segments to correct alignment issues. There are clinical examples for many long bones (e.g., femur, tibia, humerus, radius, ulna, etc.), which can be managed through corrective osteotomies to restore improved limb function. With reference to the tibia, there are proximal and distal corrective osteotomies that can address different biomechanical alignment issues.

For example, in certain embodiments the orthopedic implants described herein can comprise a wedge including a base portion and an apical portion that tapers or narrows along the length of the wedge, and which decreases in thickness relative to the base portion. At least the base portion can comprise medial and lateral lobes that are curved to approximate the cross-sectional shape of the proximal canine tibia. The wedge can include one or more openings or slots configured to receive fixation elements such as fasteners or bone screws. In use, an osteotomy can be created in the caudal aspect of the proximal tibia. The osteotomy can extend cranially and proximally at an angle to the longitudinal axis of the bone. The wedge can be inserted into the osteotomy with the apical portion positioned cranially and the base portion positioned caudally such that the portion of the tibia proximal to the osteotomy is rotated cranially by an amount corresponding to the thickness of the wedge. This can rotate the tibial plateau cranially to address injuries of the cranial cruciate ligament, particularly in dogs.

Figure 1B:
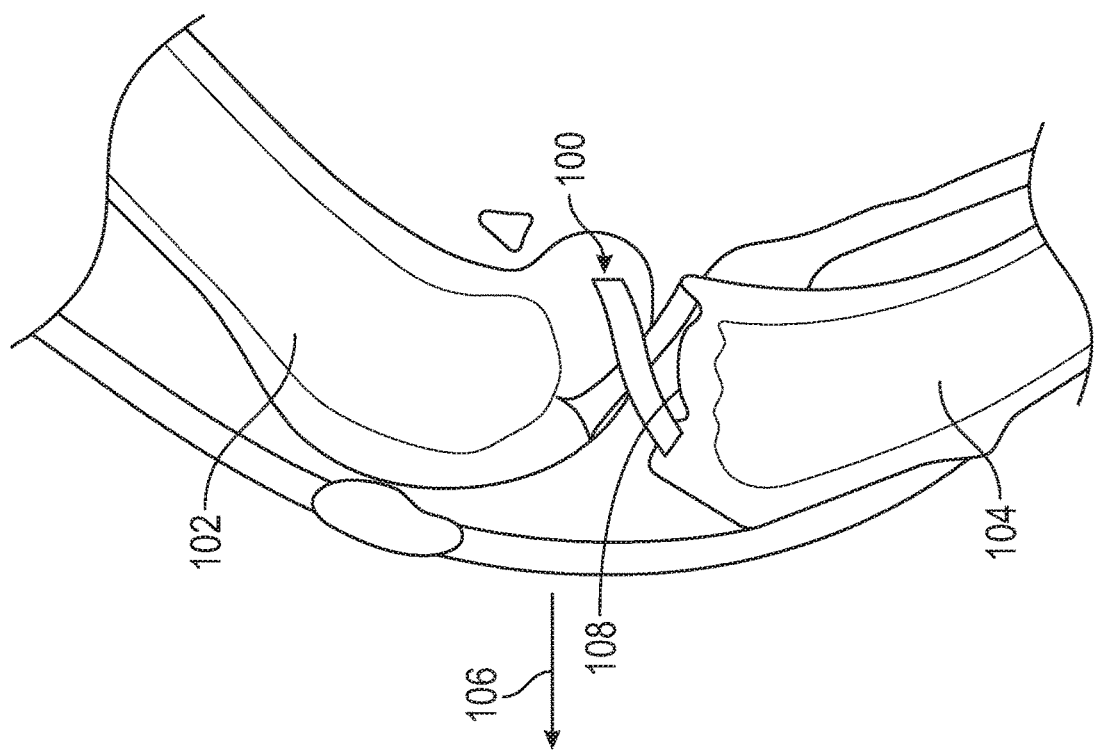

As shown in FIG. 1A, the cranial cruciate ligament 100 extends between the femur 102 and the tibia 104 and can resist advancement of the tibia in the direction indicated by arrow 106 due to force applied to the tibia by the femur. FIG. 1B illustrates forward advancement of the tibia 104 in the direction of arrow 106 due to rupture of the cranial cruciate ligament 100.

In veterinary medicine, the tibial plateau 108 can be re-positioned to, for example, address laxity and instability in the knee from a torn cranial (anterior) cruciate ligament. An orthopedic device can be implanted to re-position the tibial plateau and compensate for ruptures of the cranial cruciate ligament (for example, in dogs).

Representative orthopedic devices are shown in FIGS. 2-5, according to one embodiment. Referring now to FIGS. 2A-2C, an orthopedic implant configured as a wedge 200 can include a main body 202 having a first end portion configured as a base portion 204, a second end portion configured as an apical portion 206 extending from the base portion 204, a first surface 208, and a second surface 210 (see e.g., FIG. 3B).

Some of the figures provided herein (e.g., FIG. 3D) include an orientation system that designates the x-axis, the y-axis, and the z-axis that are orthogonal to each other. In these figures, the z-axis is oriented in the vertical direction. It should be understood that the orientation system is merely for reference and can be varied. For example, the x-axis can be switched with the y-axis and/or the orthopedic wedge 200 can be rotated. Moreover, these axes can alternatively be referred to as first, second, or third axes. For example, the x-axis can be referred to as the first axis, the y-axis can be referred to as the second axis, and the z-axis can be referred to as the third axis.

Figure 3A:
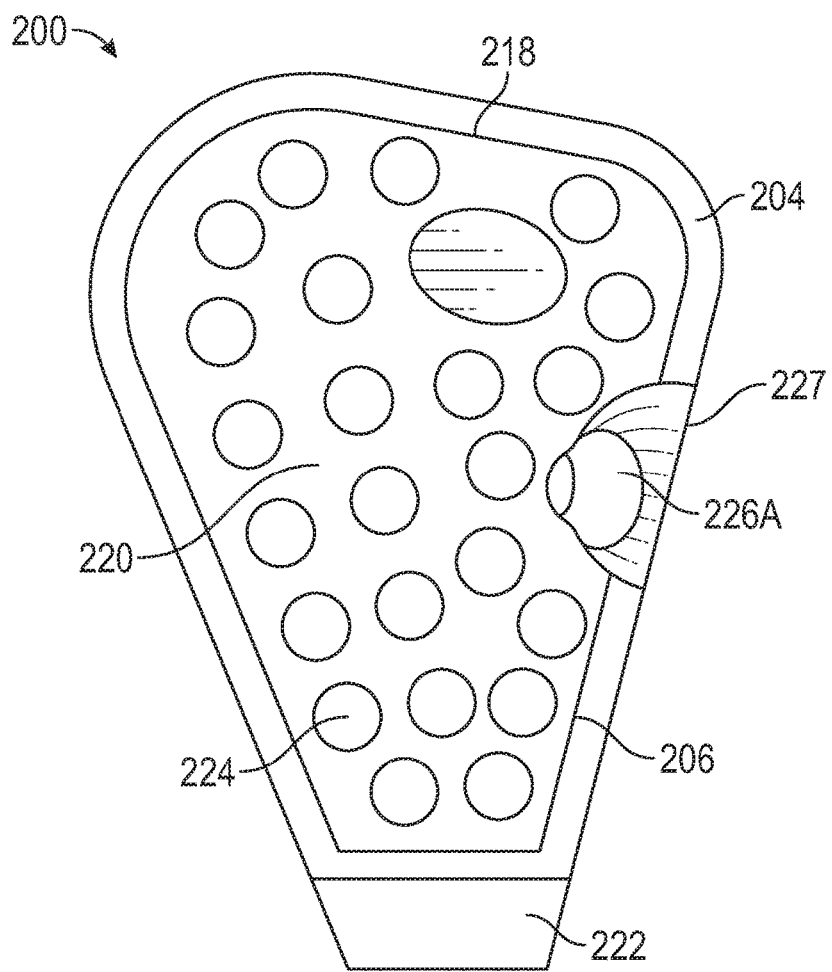
FIG. 3A illustrates a top plan view of another embodiment of an implantable orthopedic wedge.
Figure 3B:
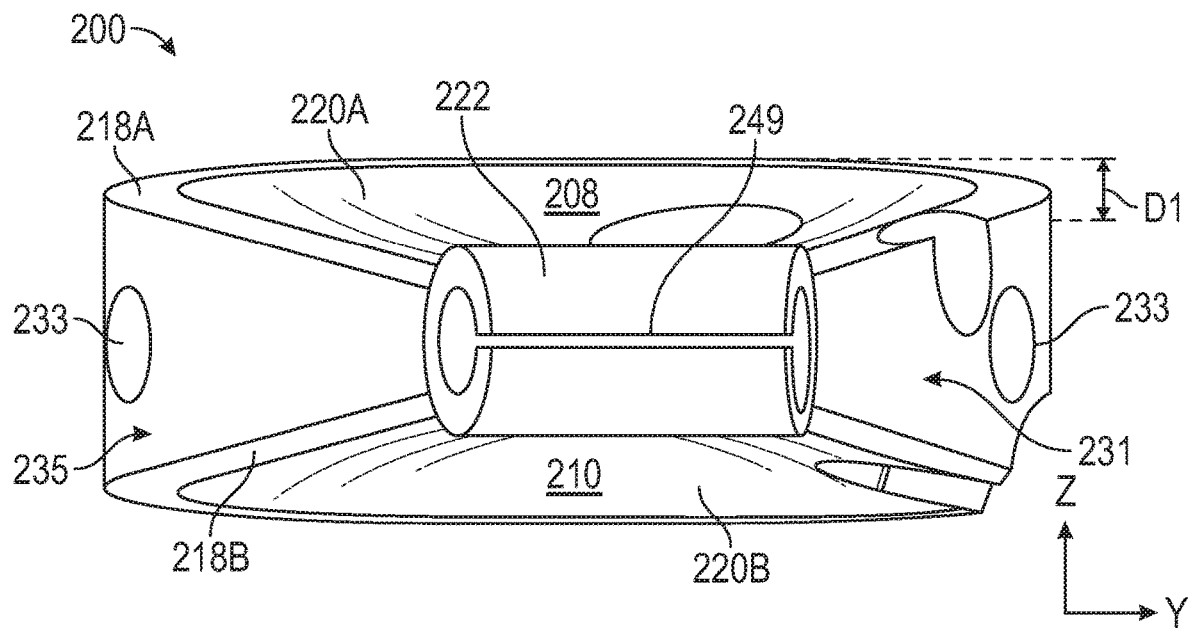
FIG. 3B illustrates an end on view of another embodiment of an implantable orthopedic wedge.
Figure 3C:
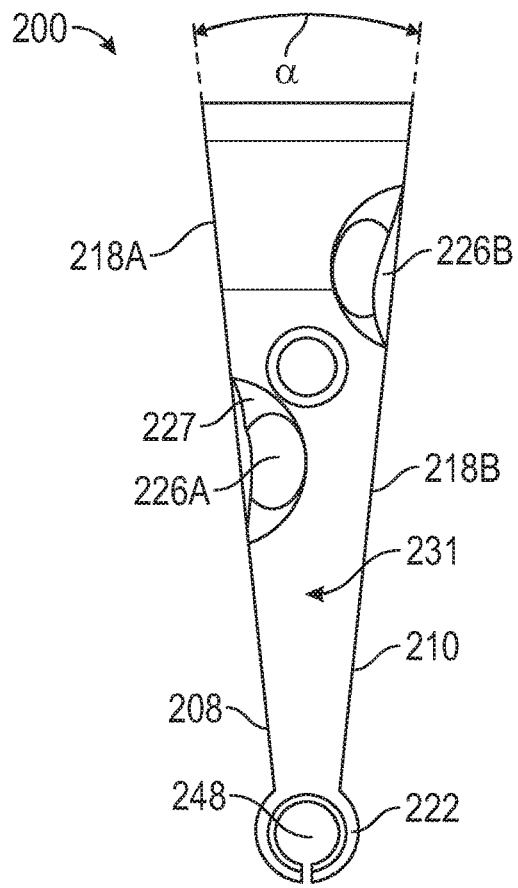
FIG. 3C is a side view of the implantable orthopedic wedge of FIG. 3B.

Referring now to FIG. 3C, the first and second surfaces 208, 210 can define a wedge angle α between them. In some embodiments, the angle α can be from 5° to 60°, 5° to 45°, 10° to 30°, etc. In particular embodiments, the angle α can be 18°. In certain embodiments, the angle α can correlate, or directly correspond, to the degree of rotation of the tibial plateau achieved when the wedge is inserted into an osteotomy formed distally of the proximal head of the tibia, as further described below. Thus, for example, in certain embodiments insertion of a wedge having an angle α of 18° can result in a cranial rotation of the plane of the tibial plateau by 18°.

Figure 3D:
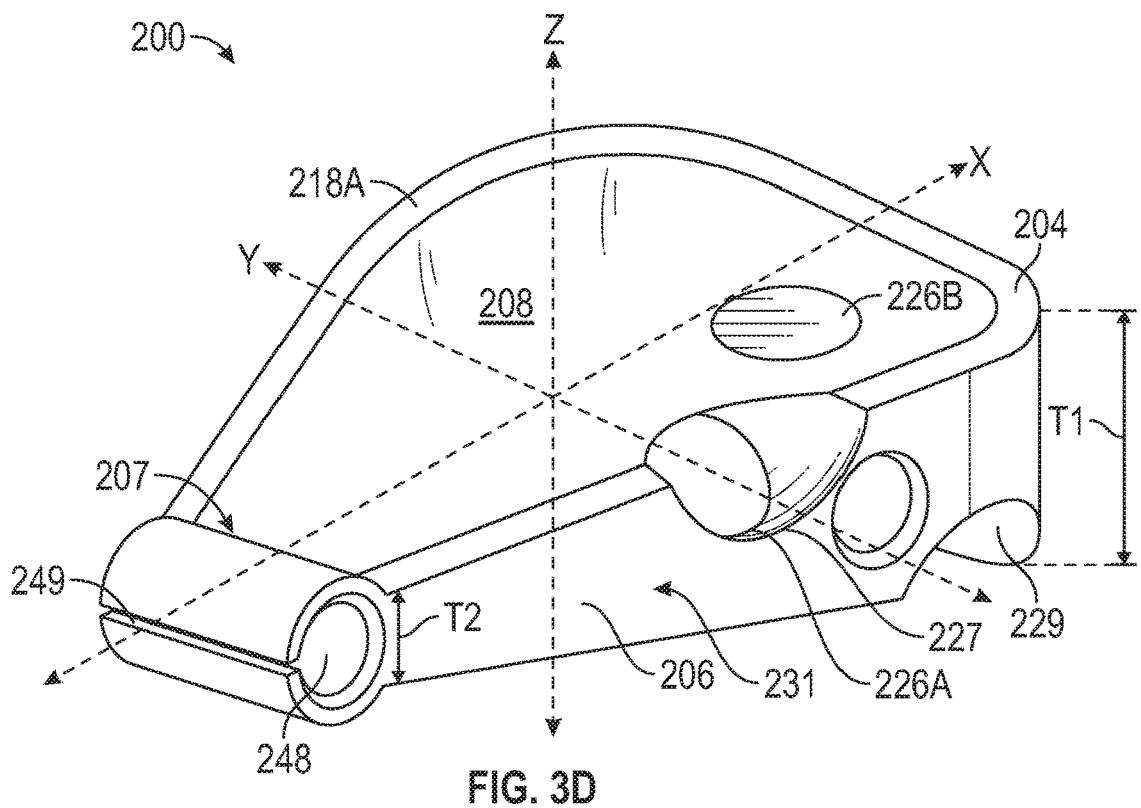
FIG. 3D is a perspective view of the implantable orthopedic wedge of FIG. 3B.

Referring to FIG. 3D, the base portion 204 can have a first thickness $T_1$ measured along the z-axis at the thickest portion of the base, and the apical portion 206 can have a second thickness $T_2$ measured along the z-axis at a cranial end 207 of the apical portion 206. In some embodiments, the first thickness $T_1$ can be greater than the second thickness $T_2$.

In some embodiments, the orthopedic wedge 200 can have an outer profile geometry that resembles a cross-section of the canine tibia just below the insertion of the caudal cruciate ligament and the medial collateral ligament. As used herein, the term "outer profile geometry" refers to the perimeter of the orthopedic wedge as seen in a plan view. Referring to FIG. 2C, in some embodiments, the main body 202 can include a first lobe portion 214 having radius $r_1$, and a second lobe portion 216 having radius $r_2$. The first and second lobes 214, 216 can be formed integrally as part of the base 204. As used herein, the terms "integrally formed" and "unitary construction" refer to a construction that does not include any welds, fasteners, or other means for securing separately formed pieces of material to each other.

In some embodiments, the first and second lobe portions 214, 216 can have differing thicknesses such that the thickness of the wedge tapers in the medial-lateral direction across the width of the base portion (e.g., along the y-axis in FIG. 3D). In other embodiments, the first and second lobe portions can be of equal thickness.

Referring now to FIG. 2A, the apical portion 206 can comprise a first straight edge 240 and a second straight edge 242 extending from the base portion and angled relative to (e.g., toward) each other. The first edge 240 can intersect the first lobe portion 214 at a vertex generally indicated at 244, and the second edge 242 can intersect the second lobe portion 216 at a vertex 246. Thus, as shown in FIG. 2A the base portion 204 can have a width $W_1$ measured, for example, along the y-axis (FIG. 3D) between the vertices 244 and 246. The apical portion 206 can have a width $W_2$ (FIG. 2A) measured along the y-axis at an end portion of the apical portion that is opposite the base portion 204. In some embodiments, the width $W_1$ can be greater than the width $W_2$ and the radius $r_1$ of the first lobe can be greater than the radius $r_2$ of the second lobe, such that the outer profile geometry of the orthopedic wedge 200 resembles a cross-section of the canine tibia.

As shown in FIG. 2B, the orthopedic wedge 200 can be made in a variety of sizes having differing main body thicknesses, widths, and wedge angles. During an implantation procedure, a surgeon can have access to multiple orthopedic wedges and select the appropriate wedge to adjust the tibial plateau angle as dictated by the anatomy of the patient.

Referring now to FIGS. 3B-3D, in certain embodiments each of the first and second surfaces 208, 210 of the orthopedic wedge 200 can have a curved or dished configuration. For example, the first surface 208 can comprise an edge or rim portion 218A extending along a perimeter of the main body, and a center portion 220A (FIG. 3A) that curves away from the rim portion in a direction toward the geometric center of the wedge. As shown in FIG. 3B, the deepest point of the center portion 220A can be offset from the edge portion 218 in a direction along the Z-axis by a distance $D_1$ such that the edge portion 218A is higher than the region within the edge portion. In some examples, the distance $D_1$ can be in the range of 0.1 mm to 1.5 mm, and more particularly in the range of 0.5 mm to 1 mm. The opposite surface 210 of the wedge can comprise a rim portion 218B and a center portion 220B configured similarly to the rim portion 218A and the portion 220A of the first surface 208.

The surfaces 208 and 210 can be configured such that, when implanted in an osteotomy as further described below, the edge portion 218A of the first surface 208 contacts an outer cortex of a proximal portion 110 of the tibia 104 that comprises the proximal surface of the osteotomy (e.g., located between the tibial plateau 108 and the tibial tuberosity 109, see e.g., FIG. 4), and such that the edge portion 218B of the second surface 210 contacts an outer cortex of a portion 112 of the tibia that comprises the distal surface of the osteotomy. In this manner, the perimeter of the implant can contact the harder, exterior cortical bone, and stresses or loads exerted on the softer, injury-prone cancellous bone can be reduced. This configuration can also help maximize stability by preventing rocking during offset loading.

The orthopedic wedge can comprise one or more non-resorbable bio-compatible materials (e.g., stainless steel, titanium, cobalt chrome, and/or tantalum). In other embodiments, in lieu of or in addition to the non-resorbable materials the orthopedic wedge can comprise one or more bioresorbable materials. Bioresorbable materials that can be used with the wedge embodiments described herein can include, but are not limited to, polycarpolactone (PCL), polyglycolide acid (PGA), polylactic acid (PLA), poly L-lactide-co-D-, L-latide (PLDLA) and biphasic calcium phosphate (BCP) (e.g., in a 70:30 ratio), polydioxanone (PDS), poly-L-lactic acid (PLLA), polyglycolic acid (PGA), hydroxyapatite PLLA (HA/PLLA), and combinations thereof. In such embodiments, after implantation of the orthopedic wedge within an osteotomy, the orthopedic wedge can be configured to resorb, dissolve, or break down inside the patient's body. The bioresorbable material can be configured to resorb or dissolve at a rate and in a pattern similar to new bone growth such that as the orthopedic wedge dissolves, new bone can grow within the osteotomy to at least partially close or fill in the osteotomy. In still other embodiments, the orthopedic wedge can comprise a combination of non-resorbable biomaterials and bioresorbable materials.

Referring to FIGS. 3A and 3B, in some embodiments, the wedge 200 can comprise a positioning member 222. The positioning member 222 can be coupled to the apical portion 206 and can extend in a medial-lateral direction when implanted. The positioning member 222 can be configured to be disposed within a corresponding opening created in the bone during implantation. This configuration can contribute to accurate implantation of the orthopedic wedge and can mitigate movement of the implant in the medial-lateral or cranial-caudal directions under load. In the illustrated embodiment, the positioning member 222 can include an opening 248 (FIGS. 3C and 3D) extending longitudinally through the member. In certain embodiments, the positioning member 222 can comprise curved upper and lower portions separated by a groove or slot 249. This can allow the diameter of the positioning member 222 to be compressed slightly when inserted into a guide opening created in a bone, as described in greater detail below.

While the illustrated embodiment includes a substantially cylindrical positioning member 222 and correspondingly shaped opening 114 in the native tibia (FIG. 9), the positioning member 222 and corresponding opening 114 can be any of various shapes, such as, without limitation, square, triangular, cruciform (cross-shaped), rectangular, hexagonal, octagonal, etc.

Referring again to FIG. 3A, in some embodiments, the main body 202 can have a plurality of openings 224 extending through the main body of the wedge. In this embodiment, one or more openings 224 are configured as anchor openings 226 providing a lumen through which one or more anchor elements (e.g., screws 228 in FIGS. 5A and 5B) can pass to couple the orthopedic wedge to the surrounding bone, as discussed in more detail below.

In some embodiments, as shown in FIG. 3C, the orthopedic wedge can have first and second anchor openings 226A and 226B extending at an angle through the main body 202 of the wedge 200. For example, the opening 226A extends at an angle from the rim portion 218A of the second side edge 242 on the surface 208 through the body of the wedge to the surface 210 in a direction generally toward the surface 210 and toward the first side edge 240. The opening 226B extends from the rim portion 218B on the same side of the wedge as the edge 242 but on the surface 210, and through the surface 208 in a direction generally toward the surface 208 and toward the edge 240. The wedge can also comprise an opening 233 extending through the body from a side surface 231 to a side surface 235 on the opposite side of the apical portion 206 from the surface 231.

Figure 5B:
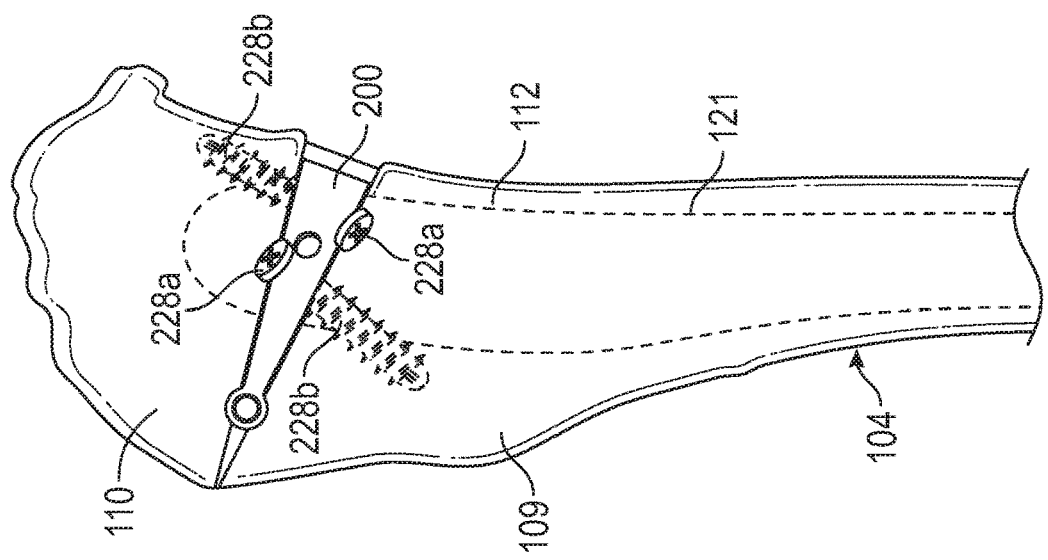
FIG. 5B illustrates a lateral view of an orthopedic wedge implanted within a tibia.
Figure 5A:
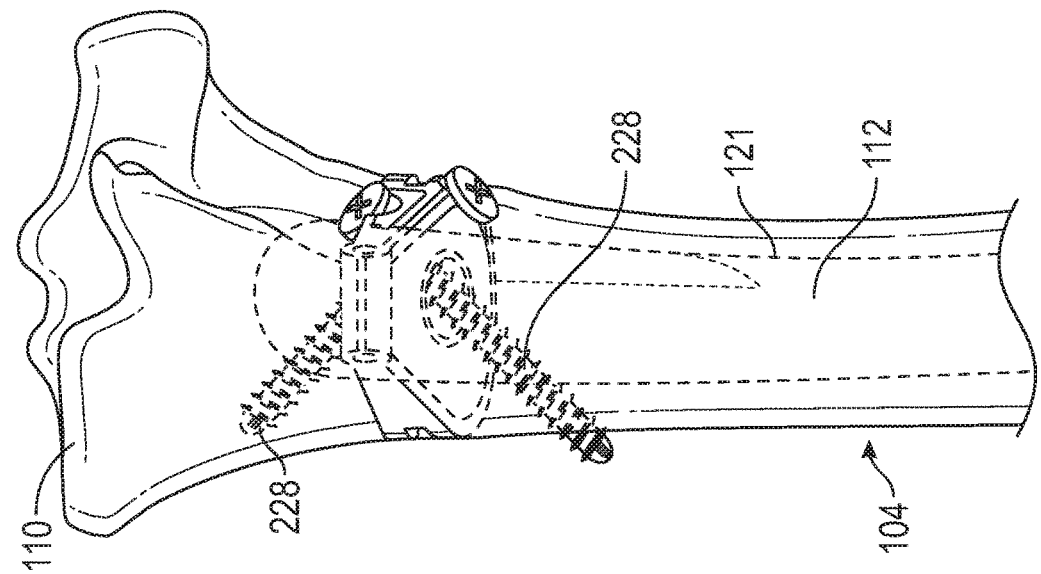
FIG. 5A illustrates a cranial view of an embodiment of an orthopedic wedge implanted within a tibia.

Referring now to FIGS. 5A and 5B, the anchor openings 226A and 226B can be configured such that one or more anchor elements, for example, screws 228 having head portions 228a and threaded shanks 228b, can extend through the anchor openings 226 and couple or anchor the orthopedic wedge to the surrounding bone. The head portions 228a of the screws 228 can be configured to abut the main body 202 of the wedge and the body portions 228b can be configured to extend into portions of the surrounding bone. The screws can be configured to extend through the central marrow chamber 121 of the tibia 104 and into the harder cortical bone, to firmly anchor the wedge therein.

In the illustrated configuration, one or both of the openings 226A and/or 226B can be countersunk to accommodate the heads 228a of the screws. For example, in the illustrated embodiment the opening 226A can comprise a countersunk portion 227. As best shown in FIGS. 2A and 3D, the countersunk portion 227 can comprise walls that curve or slope inwardly from the surface 208 and from the side surface 231 of the wedge toward the opening 226A. Referring to FIGS. 3C and 3D, the opening 226B can also include a countersunk portion 229 that slopes or curves inwardly toward the opening 226B from the surface 210 and from the surface 231. In some embodiments, the anchor elements can be smooth pins.

The angle at which the anchor openings 226 extend through the body of the wedge can vary. In some embodiments, the angle can be from 10° to 90°, from 10° to 45°, or from 5° to 40°. In a representative embodiment, the openings 226 can extend through the main body at an angle of 15° to 25° relative to a plane defined by the y-axis and the z-axis of FIG. 3D.

Returning to FIG. 3A, in certain embodiments, the openings 224 can be configured as ossification openings defining a lumen into which one or more biologics (e.g., bioglass, bone morphogenetic protein (BMP), and/or sclerostin) can be disposed to enhance bone formation. The ossification openings can also be configured to promote bone tissue growth into the main body of the implant.

While the illustrated embodiment shows the ossification openings and the anchor openings 226 as having a substantially round cross-sectional shape, and the lumina as having correspondingly cylindrical shapes, the shape of the openings and the lumina can be any of various shapes, including but not limited to square, hexagonal, triangular, cruciform, ovular, etc.

In particular embodiments, the thicknesses $T_1$, $T_2$ of the orthopedic wedge can be in the range of 1 mm to 15 mm, and more particularly in the range of 4 mm to 10 mm, with 6 mm and 8 mm being specific examples; the widths $W_1$ and $W_2$ can be in the range of 1 mm to 45 mm, more particularly in the range of 5 mm to 30 mm, with 8 mm and 24 mm being specific examples; and the wedge angle α can be in the range of 5° to 40°, and more particularly in the range of 10° to 20° or 15° to 25°, with 13° and 18° being specific examples, depending upon factors such as the breed, size, weight, etc., of the animal.

Figure 4:
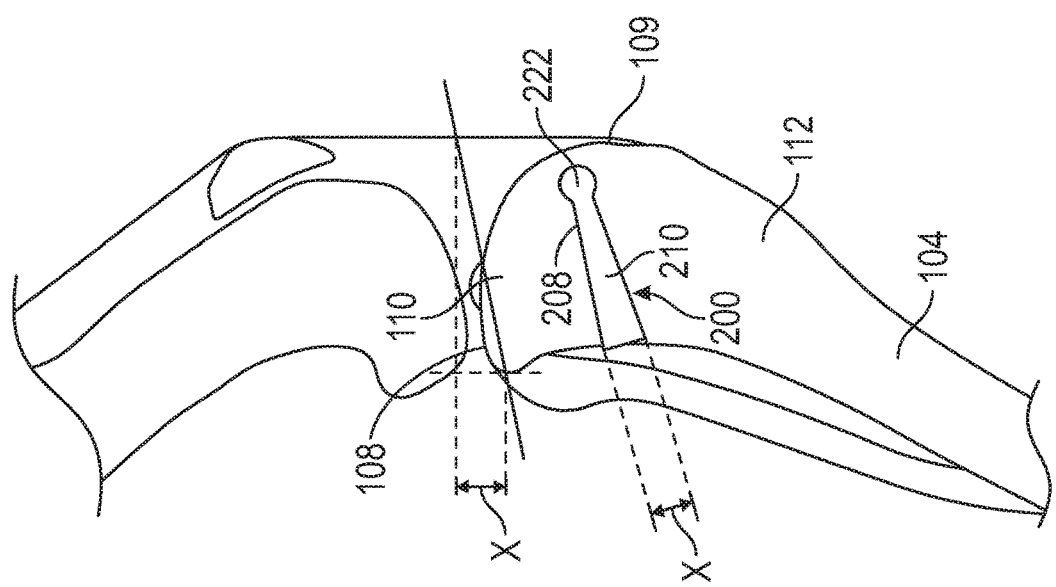
FIG. 4 illustrates an embodiment of an orthopedic wedge implanted within a tibia to change the angle of the tibial plateau.

Referring now to FIGS. 4-5, generally, the orthopedic wedge 200 can be implanted within a bone of a patient by drilling a hole into the bone, performing or creating an osteotomy (e.g., a straight-cut osteotomy, a radially curved osteotomy, and/or a spherical cut osteotomy), expanding the osteotomy, implanting the orthopedic wedge, and anchoring the wedge in place using an anchoring element. The cut is made in the proximal caudal aspect of the tibia 104 at a location on the tibial shaft between the cranial border and the tibial tuberosity, and is angled proximally toward the tibial tuberosity. As shown in FIG. 4, the cut can thereby define a pivot point about which the portion 110 of the tibia 104 can pivot to expand the osteotomy. The orthopedic wedge 200 can be implanted within the osteotomy to adjust the angle of the tibial plateau 108 by rotating the tibial plateau cranially from a first position to a second position. For example, with reference to FIG. 4, in certain embodiments there can be a direct relationship between the thickness of the base portion of the implant and the corresponding displacement of the tibial plateau when the implant is inserted into the osteotomy. For example, FIG. 4 illustrates implantation of a wedge 200 with base thickness X, which results in the proximal portion 110 of the tibia being pivoted upwardly by the distance X, and a corresponding rotation of the tibial plateau 108 to a selected angle with respect to the femur.

Prior to the procedure, a surgeon can select the desired size of orthopedic wedge for implantation based upon, for example, the size, breed, age, etc., of the animal. The surgeon can also select the size and/or shape of the wedge based at least in part on the size and shape of the cross section of the tibia, and/or the selected angle to which it is desired to adjust the tibial plateau. The orthopedic wedge can be used to adjust the angle and/or position of the tibial plateau in the cranial caudal direction, the medial-lateral direction, and/or the ventral-dorsal direction. In some embodiments, the orthopedic wedge can be used to adjust the angle of the tibial plateau in the medial-lateral direction in order to correct angular deformities in the limb of the patient.

Figure 7:
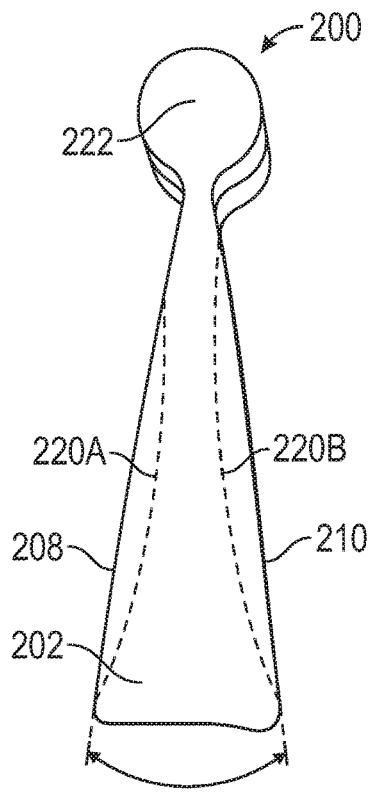
FIG. 7 illustrates a side view of the implantable orthopedic wedge of FIG. 6A.
Figure 8:
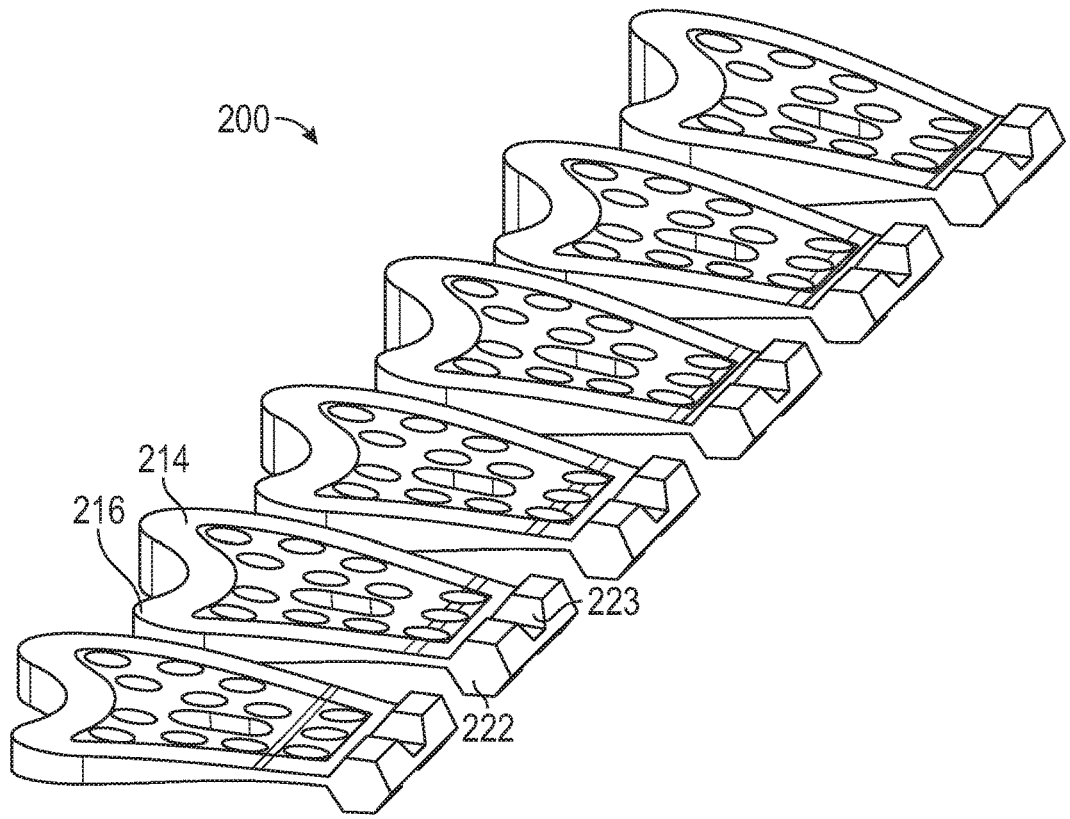
FIG. 8 illustrates a perspective view of a plurality of the implantable orthopedic wedges of FIG. 6 in various sizes.

FIGS. 6A, 7, and 8 illustrate another embodiment of the orthopedic wedge 200 (configured for the left tibia) wherein the base portion 204 has an outer perimeter (e.g., profile) that closely matches the cross-sectional perimeter of a native tibia 104. As shown in FIG. 7, the first and second surfaces 208, 210 of the wedge 200 can have a concave or dished configuration, wherein each surface 208, 210 can each comprise a respective edge or rim portion 218A, 218B (see e.g., FIG. 3A) extending along a perimeter of the main body 202, and a respective center portion 220A, 220B that curves away from the rim portion in a direction toward the geometric center of the wedge.

As shown in FIG. 8, the orthopedic wedge 200 can be made in a variety of sizes having differing main body thicknesses, widths, and wedge angles. During an implantation procedure, a surgeon can have access to multiple orthopedic wedges and select the appropriate wedge to adjust the tibial plateau angle as dictated by the anatomy of the patient. In some embodiments, as shown, the positioning member 222 can have a hexagonal cylinder shape including a notch 223.

Referring now to FIGS. 6B and 6C, a tibia 104 includes a tibial plateau 108, a tibial tuberosity 109 (an oblong elevation on the cranial aspect of the tibia), a lateral condyle 111 (see FIG. 6C), a medial condyle 115, and a cranial border. FIG. 6C shows a cross-sectional view of the proximal portion (e.g., the upper portion in the orientation shown in FIG. 6B) of the tibia 104 taken along line x-x of FIG. 6B representative of an osteotomy location for implanting the wedge configurations described herein. In the illustrated embodiment, the cross-section can be taken at an angle of 45° relative to the longitudinal axis of the tibia and passing near or through the tibial tuberosity 109. The perimeter of the native tibia 104 at the location of the cross-section is defined by the medial condyle 115 (which extends from the medial surface of the tibia, and which can be approximated as a compound curve defined by first and second circles 123 and 125 having first and second radii $r_3$ and $r_4$). The perimeter can be further defined by and the lateral condyle 111 (which extends from the lateral surface of the tibia, and which can be approximated as a circular portion 127 having radius $r_5$). The lateral and medial condyles 111, 115 define a popliteal notch 117 between them on the caudal surface of the tibia. The curvature of the popliteal notch 117 can be approximated by a circle 129 having a radius $r_6$.

Referring again to FIG. 6A, the base portion 204 of the wedge 200 can have a similar cross-sectional shape to the native tibia 104, including a first lobe portion 214 and a second lobe portion 216. For example, the first lobe portion 214 can comprise a curved portion 215 comprising the radius $r_3$ of the circle 125 of FIG. 6C, and a curved portion 217 extending from the portion 215 and comprising the radius $r_4$ of the circle 123. The first and second lobe portions 214, 216 can define a recessed portion or notch 232 between them. The notch 232 can be configured to align with the popliteal notch 117 when the wedge 200 is implanted within the tibia 104. The notch 232 can have a depth $D_2$ measured from a lower-most (e.g., caudal-most) edge of the first lobe 214 (FIG. 6A) and extending in a direction cranially along the x-axis (FIG. 3D).

The wedge 200 can have a first edge 241 and a second edge 243 extending from the first and second lobe portions 214, 216 and angled relative to (e.g., toward) each other. The first edge 241 can be substantially straight until it intersects the first lobe 214, and the second edge 243 can have a curved shape that mimics the curved lateral surface 119 (see e.g., FIG. 6B) of the native tibia 104. As shown in FIG. 6C, the curved lateral surface of the native tibia 104 can be approximated by a circle 131 having radius $r_7$. Thus, at least a portion of the edge portion 243 of the wedge can be curved according to the radius $r_7$ in order to approximate the curvature of the lateral surface of the tibia at that location. Mimicking the cross-sectional shape of the native tibia allows the edge portions of the wedge 200 to contact the harder, exterior cortex of the tibia, mitigating stress exerted on the softer, injury-prone cancellous bone, and reducing overhang of the implant beyond the area of the bone. The general outline of the wedge 200 of FIG. 6A is shown superimposed on the cross-section of the tibia in FIG. 6C.

Returning to FIG. 6A, in some embodiments, the implant can also include an elongated opening or slot 250 defined in the apical portion 206 and configured to receive one or more anchor elements such as one or more screws. The wedge 200 can also comprise a plurality of openings 251 configured to receive any of a variety of therapeutic agents and/or to promote bone growth into the wedge, depending upon the particular application.

FIGS. 9-15 show a representative method of implanting a wedge within, for example, a tibia 104 of a patient to adjust the angle of the tibial plateau 108 that can be used in combination with any of the wedge embodiments described herein. Referring to FIG. 9, a surgeon can drill a tubercle opening 114 through the tubercle of the tibia 104 in a location below (e.g., distal to) the site of the patellar ligament attachment such that the opening 114 is caudal to, and distal to, the patellar ligament attachment site. The tubercle opening 114 can extend through the tibia 104 in a medial-lateral direction, and the angle of the tubercle opening 114 can be parallel to the joint line between the femur and the tibia. As used herein, unless stated in absolute terms such as "completely parallel," the term "parallel" includes the term "substantially parallel." For example, an object is substantially parallel with respect to a reference object or plane when the object is oriented at an angle of ±20° or less with respect to the reference object or plane. In some embodiments, the tubercle opening 114 can be 4 mm in diameter. In some embodiments, a 4 mm bridge 116 of bone can be left between the tubercle opening 114 and the cranial edge of the tibia (e.g., at or near the tibial tuberosity).

Referring to FIG. 10, a saw guide 300 can be used to align a saw blade for performance of an osteotomy. The saw guide can comprise a first member 301 and a second member 303 mounted or fixed to a tibia 104 with the second member 303 positioned against the tibia 104, and the first member 301 positioned over top of the second member 303. The first member 301 and the second member 303 can be assembled together with the second member 303 oriented at an angle (e.g., perpendicular) to the first member 301. The first member 301 can have a guide opening 302 defined in one end portion of the member, and configured to align with the tubercle opening 114. A guide channel 304 can extend from the guide opening 302, and can be configured to allow a saw blade to extend through the channel.

Figure 12:
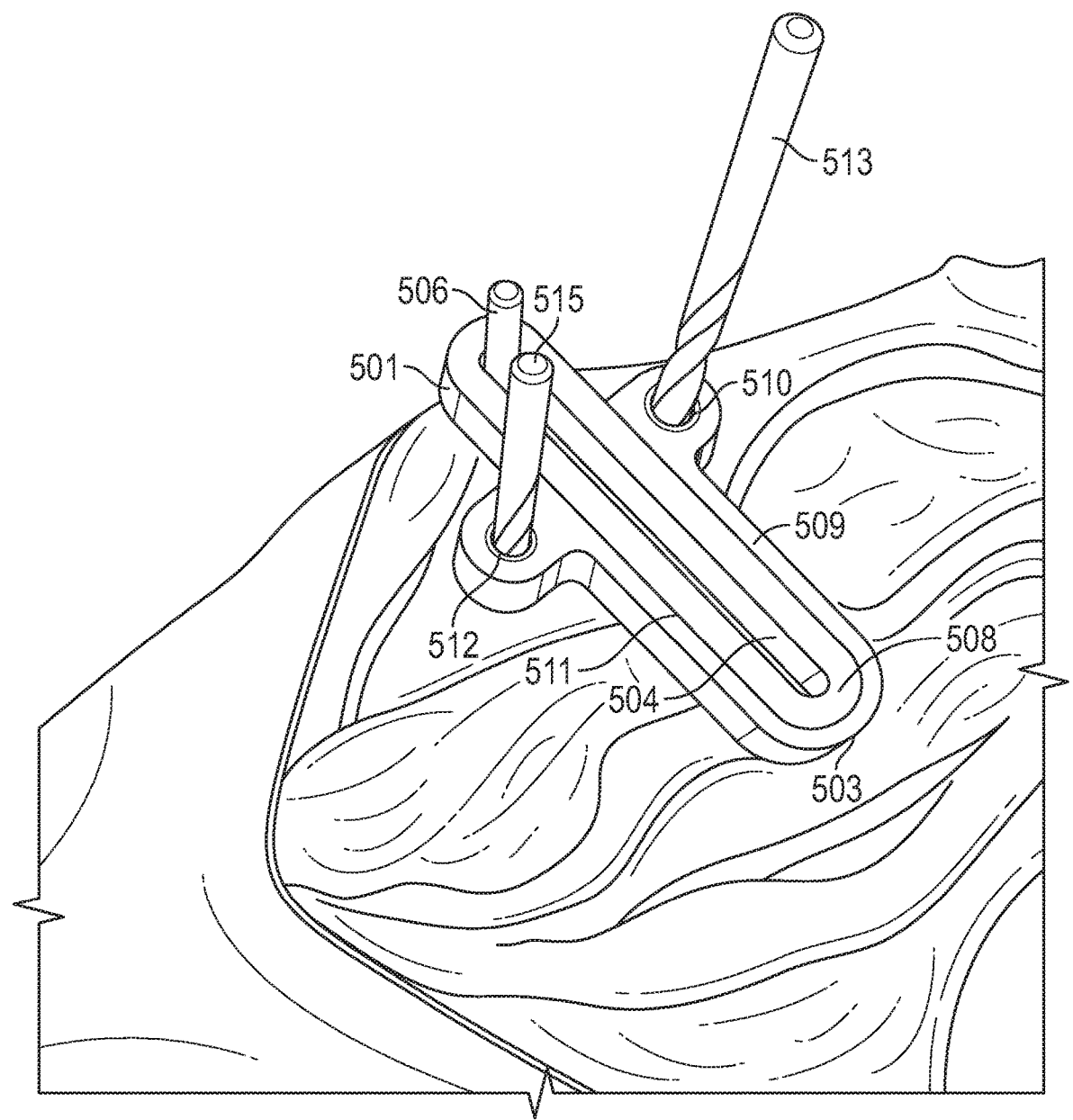

FIGS. 11A, 11B, and 12 illustrate another configuration of a saw or osteotomy guide 500. The guide 500 can comprise a first member 501 shown in FIG. 11A, and a second member 503 shown in FIG. 11B. Referring to FIG. 11A, the first member 501 can comprise a guide opening 502 defined in one end portion of the member, and a guide channel 504 can extend from the guide opening 502. The opening 502 can be configured to be aligned with the opening 114 in the tibia, and the guide channel 504 can be configured to allow a saw blade to extend through the channel similar to the embodiment of FIG. 10. Referring to FIG. 11B, the second member 503 can comprise a U-shaped member including a first arm portion 509 and a second arm portion 511 coupled together at one end by a curved third portion 524, and extending therefrom. The second member 503 can have stabilizer openings 510, 512 be defined in the first arm portion 509 and the second arm portion 511, respectively, on opposite sides of the guide channel 504 from each other. The assembled saw guide 500 can be releasably coupled to the tibia 104 by aligning the guide opening 502 of the first member 501 with the tubercle opening 114 in the tibia, and inserting a pin 506 through the guide opening 502 and into the tubercle opening 114.

In some embodiments, as shown in FIGS. 11-12, the second member 503 of saw guide 500 can comprise first and second arms 509, 511 that define a u-shaped opening. In such embodiments, each arm 509, 511 can comprise a respective stabilizer opening 510, 512. The second member 503 can be configured to be coupled to the first member 501 (e.g., by sliding engagement), such that the first member 501 is disposed within the u-shaped opening (see FIG. 12). This allows the first and second members 501, 503 of the saw guide 500 to be coupled to the tibia independently of one another, such that the first and/or second member 501, 503 can be used independently or in combination during the implantation procedure.

FIG. 12 illustrates the assembled saw guide 500 in place on the tibia. With the saw guide 500 coupled to the tibia 104, a caudal end portion 508 of the saw guide 500 can be pivoted relative to the guide opening 502 such that the guide channel 504 is disposed below (e.g., distal to) the insertion site of the native caudal cruciate ligament.

Once the guide channel 504 is adjusted to the selected position, first and second fixation openings (not shown) can be drilled through the first and second stabilizer openings 510, 512. First and second stabilizer pins 513, 515 (FIG. 12) can extend through the first and second stabilizer openings 510, 512 and into the first and second fixation openings to stabilize the saw guide 500 during sawing of the osteotomy.

Figure 13:
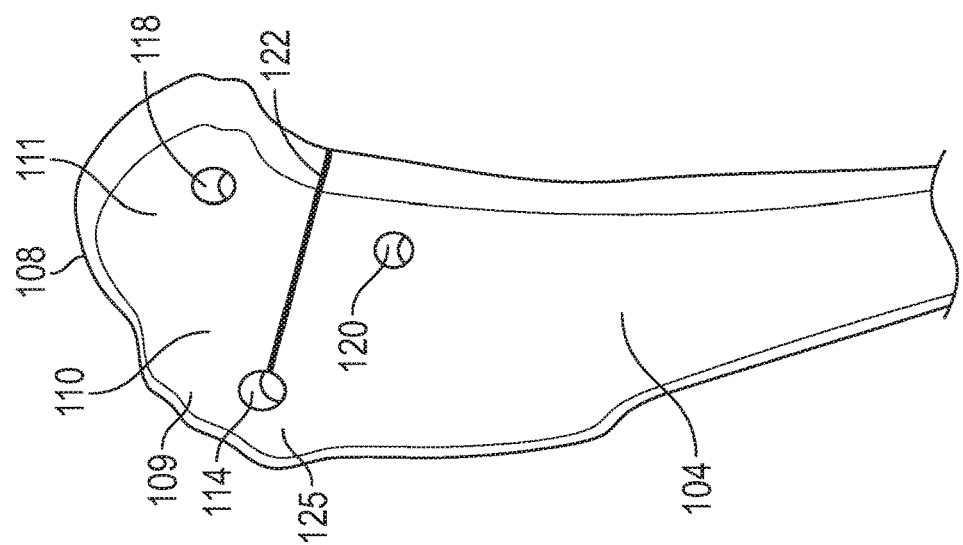

The surgeon can use a saw (e.g., a saw having a blade 0.025" thick) to cut an osteotomy 122 along the guide channel 504. Once the osteotomy is substantially complete, the surgeon can remove the saw guide 500 and complete the osteotomy by extending the cut into the tubercle opening 114, as shown in FIG. 13.

In some embodiments, the osteotomy 122 can extend partially but not completely through the tibia, thereby creating a bone portion or "bridge" located, for example, adjacent the tibial tuberosity 109. The osteotomy 122 can thereby define a pivot point 125 about which the portion 110 of the tibia 104 can pivot to expand the osteotomy 122 and rotate the tibial plateau 108 cranially.

The osteotomy 122 can be a substantially straight cut located ventral to the native insertion sites of the caudal cruciate ligament and the medial collateral ligament. This location mitigates the risk of soft tissue damage such as, for example, cutting the caudal cruciate and medial collateral ligaments. Furthermore, the osteotomy location mitigates surgical trauma to the patient, thus minimizing recovery time, because the joint capsule does not need to be incised.

Figure 14:
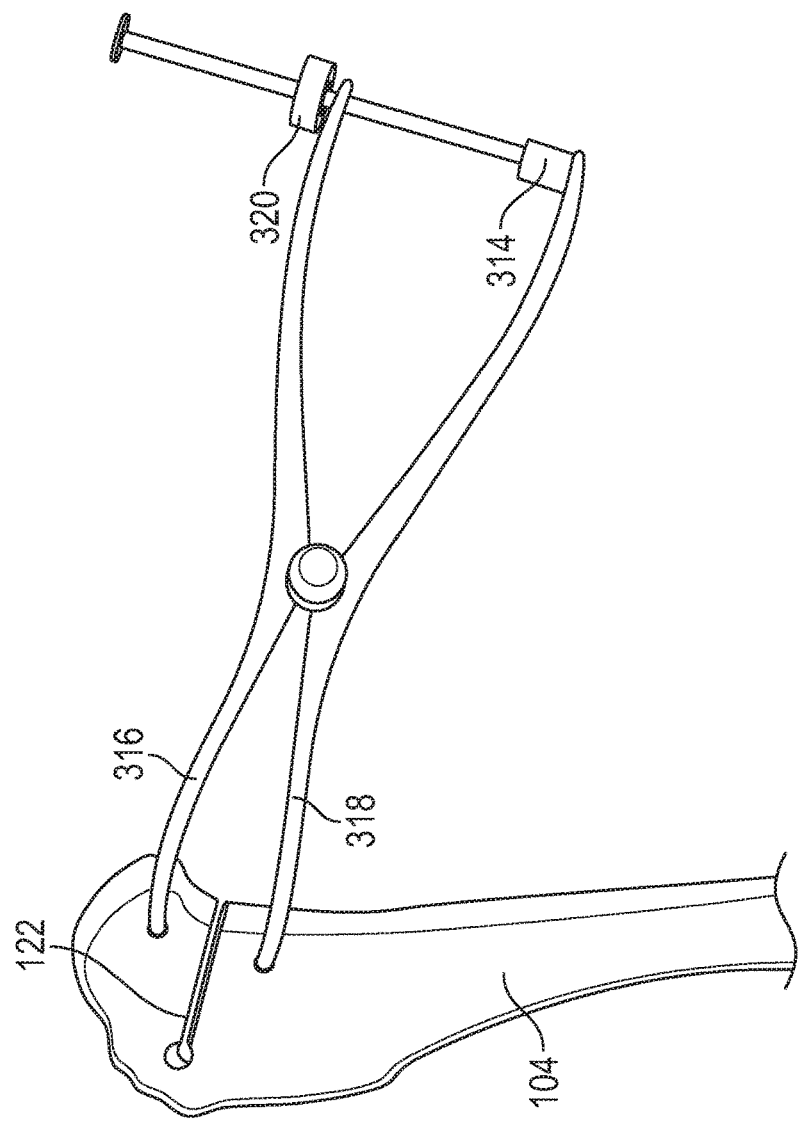
Figure 15:
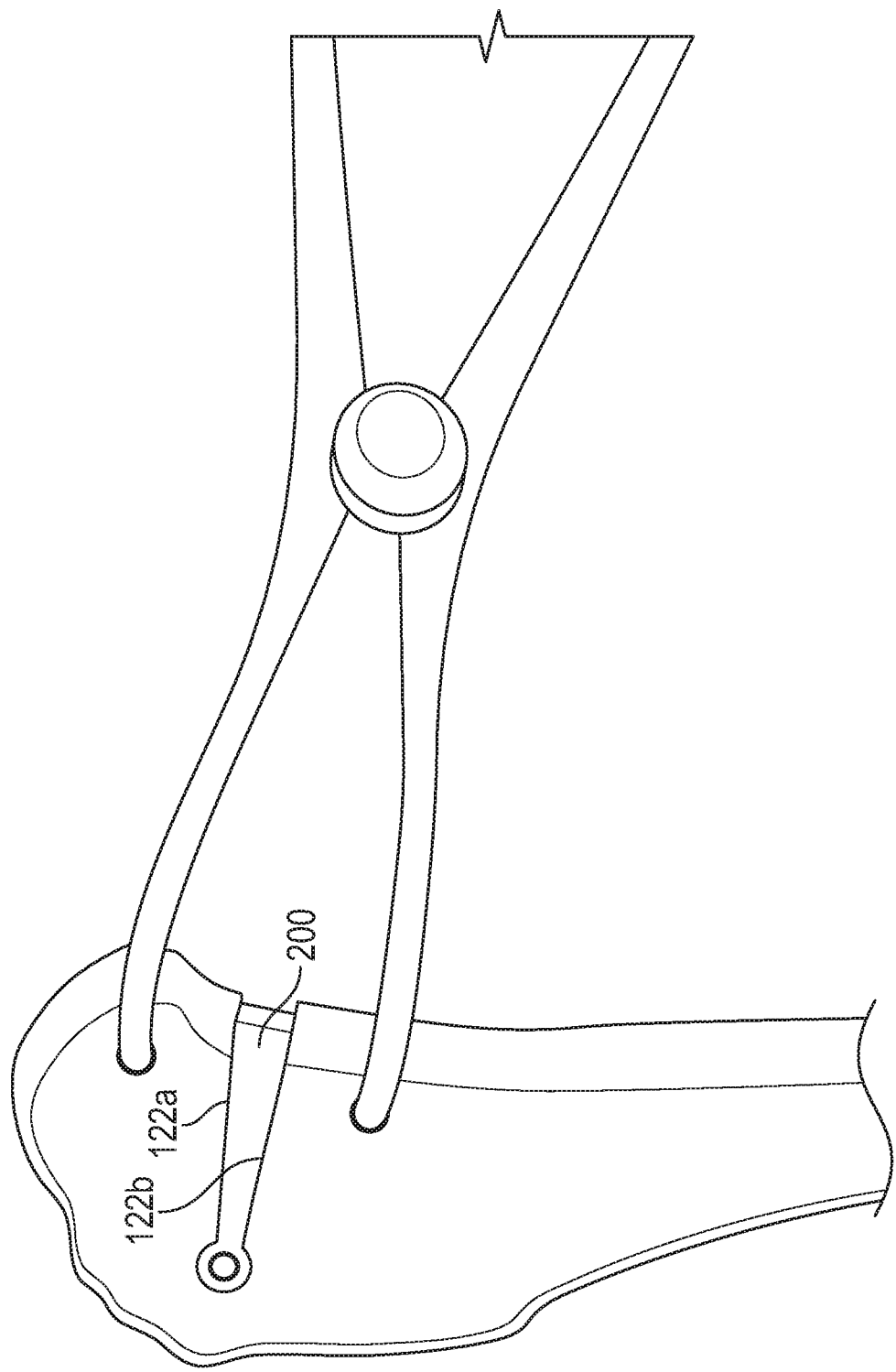

Referring now to FIG. 14, the surgeon can use an expander 314 to expand the osteotomy 122. The expander can have first and second arms 316, 318 and an adjustable portion 320 actuatable to move the first and second arms away from one another. The surgeon can dispose the first and second arms 316, 318 of the expander within the first and second fixation openings 118, 120 and actuate the adjustable portion 320 to expand the osteotomy 122. The osteotomy 122 can be expanded to a size such that the orthopedic wedge 200 can be disposed within the osteotomy 122, as shown in FIG. 15. Both the osteotomy and the orthopedic wedge can be located below (e.g., distal in the orientation shown in FIG. 15) the insertion site of the medial collateral ligament and the insertion site of the caudal cruciate ligament.

In some embodiments, prior to inserting the orthopedic wedge 200, the surgeon can dispose a trial wedge sized to correspond with the orthopedic wedge 200 within the osteotomy 122 to evaluate whether the osteotomy is properly sized to receive the orthopedic wedge. The trial wedge can comprise a plastic material. The trial wedge can be used to verify that the tibial plateau is being rotated by the selected amount prior to insertion of the orthopedic wedge 200.

In some embodiments, the positioning member 222 of the orthopedic wedge 200 can be disposed within the tubercle opening 114 to prevent movement of the orthopedic wedge within the osteotomy 122 in the medial-lateral and/or cranial-caudal directions. This method of implantation helps with accurate locating of the orthopedic wedge and mitigates movement of the orthopedic wedge under load.

As shown in FIG. 15, once the orthopedic wedge 200 is disposed within the osteotomy 122, the expander 314 may be released and first and second interior surfaces 122a, 122b of the osteotomy can abut the orthopedic wedge such that the edge portions 218A and 218B of the orthopedic wedge 200 contact the outer cortex of the native bone. Referring again to FIGS. 5A and 5B, the orthopedic wedge can then be coupled to the bone using, for example, one or more screws, such as first and second screws 228. To anchor the wedge during implantation, the screws 228 can be inserted through the anchoring openings such that the head portions 228a of the screws abut the main body 202 of the wedge, and the threaded body portions 228b of the screws extend into the portions 110, 112 of the native tibia 104. The screws 228 can be tightened, compressing the surrounding bone against the orthopedic wedge. In other embodiments, a single screw may be used to anchor the wedge.

In some embodiments, the one or more screws can be inserted extracapsularly, mitigating trauma from the surgical procedure. In such embodiments, the screw can be inserted through a medial surface of the tibia, and the screw can extend through the wedge in a proximal and cranial direction. In other embodiments, the screws can be inserted intracapsularly, extending through the insertion site of the cranial cruciate ligament.

Situating the orthopedic wedge within a lower straight osteotomy, as described above, allows the wedge to be predominantly loaded in compression and allows the orthopedic wedge to cap the osteotomy closely, establishing contact between the edges of the main body and the cortical wall of the tibia. This assists in stress distribution and helps prevent rocking of the dorsal tibial bone segment.

FIGS. 18-21 illustrate another embodiment of the orthopedic wedge 200 where, in lieu of or in addition to the anchor openings 226 of FIGS. 2A-3D, the orthopedic wedge comprises a fixation member 260 for anchoring the orthopedic wedge within an osteotomy (e.g., osteotomy 122). The main body of the orthopedic wedge 200 is shown schematically in FIGS. 18-21 for purposes of illustration, and can be configured according to any of the embodiments described above.

In some embodiments, such as the embodiment of FIG. 19, the fixation member 260 can be coupled to a side surface 262 of the orthopedic wedge. The length of the fixation member can extend along the z-axis, and at an angle to the longitudinal axis of the bone when implanted. In some embodiments, the fixation member 260 can be coupled to the side surface 262 such that the fixation member is parallel to the thickness dimension of the orthopedic wedge. In other embodiments, the fixation member 260 can be coupled to the side surface 262 at an angle, for example, to follow a native angle of the bone, or to align with an anatomical structure of the bone or soft tissue attached on or surrounding the bone.

The fixation member 260 can be configured to receive one or more anchoring elements to anchor the wedge to an implantation site in a bone (e.g., the tibia 108). In some embodiments, the fixation member 260 can be formed separately from the orthopedic wedge 200 and can be coupled thereto via, for example, welding, adhesives, mechanical means such as screws, etc. In other embodiments, the fixation member 260 can be formed integrally with the main body 202 of the orthopedic wedge 200.

In some embodiments, both the orthopedic wedge 200 and the fixation member 260 can comprise one or more bioresorbable materials (such as the bioresorbable materials discussed above). In other embodiments, both the orthopedic wedge 200 and the fixation member 260 can comprise one or more non-resorbable materials (such as the porous biocompatible materials discussed above). In still other embodiments, the fixation member 260 can comprise one or more non-resorbable materials and the orthopedic wedge 200 can comprise one or more bioresorbable materials, or vice versa.

Referring to FIG. 19, the fixation member 260 can comprise a first end portion 264 and a second end portion 266. The first and second end portions 264, 266 can extend beyond the thickness of the orthopedic wedge. For example, the fixation member 260 can be configured such that when implanted, the first end portion 264 can be disposed adjacent to the portion of the tibia 104 above (e.g., proximal to) the osteotomy 122, and the second end portion 266 can be disposed adjacent to the portion of the tibia 104 below (e.g., distal to) the osteotomy 122. The first and second end portions 264, 266 of the fixation member 260 can have first and second apertures 268, 270, respectively. The apertures 268, 270 can extend through the thickness of each respective end portion 264, 266. Each aperture 268, 270 can be configured to receive an anchoring element, such as a screw. In some embodiments, the apertures can extend in a direction perpendicular to the length of the fixation member 260. As used herein, unless stated in absolute terms such as "completely perpendicular," the term "perpendicular" includes the term "substantially perpendicular." For example, an object is substantially perpendicular with respect to a reference object or plane when the object is oriented at an angle between 110° and 70° with respect to the reference object or plane. In other embodiments, the apertures 268, 270 can extend at respective angles through the thickness of each respective end portion 264, 266.

The orthopedic wedge 200 can be coupled to the bone (e.g., the tibia 104) using one or more anchoring elements. The anchoring elements can be, for example, screws or pins. In some embodiments, the anchoring elements can comprise one or more bio-compatible materials. In other embodiments, the anchoring elements can comprise one or more bioresorbable materials.

Figure 22:
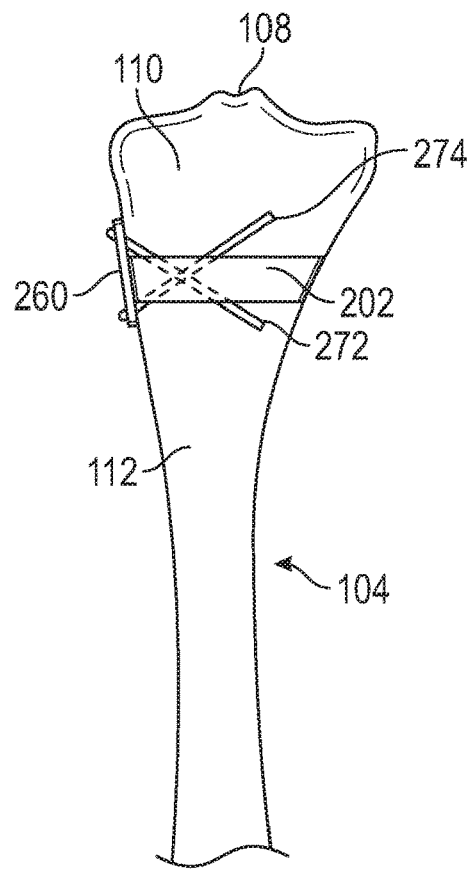
FIG. 22 illustrates a caudal view of another embodiment of an orthopedic wedge implanted within a tibia.
Figure 23:
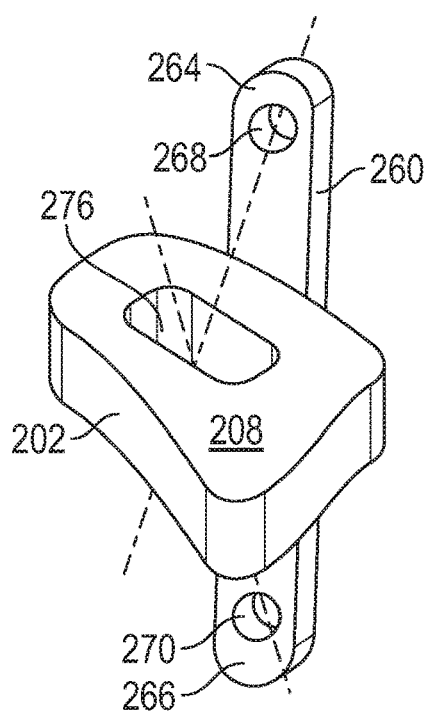
FIG. 23 illustrates a perspective view of the orthopedic wedge of FIG. 22.
Figure 24:
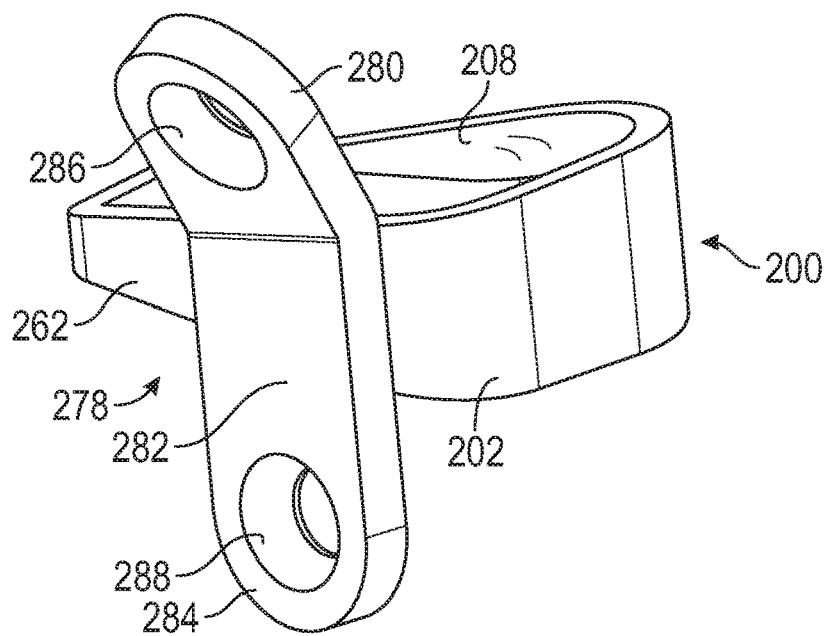
FIG. 24 illustrates a perspective view of another embodiment of an orthopedic wedge.

The anchoring elements can extend through the first and/or second apertures 268, 270. In some embodiments, a first screw 272 can extend through the first aperture 268 and into a proximal portion 110 of the tibia, and a second screw 274 can extend through the second aperture 270 and into a portion 112 of the tibia that is distal to the osteotomy, anchoring the wedge 200 to the bone. In other embodiments, as shown in FIG. 23, the orthopedic wedge 200 can comprise a central slot 276 extending through the main body 202 of the wedge. Referring now to FIG. 22, the first screw 272 can extend through the first aperture 268, through the central slot 276, and into the portion 112 of the tibia. The second screw 274 can extend through the second aperture 270, through the central slot 276, and into the portion 110 of the tibia. This configuration allows the wedge to be tightened against the bone in both directions, improving initial stability, and compressing the wedge against the bone.

In some embodiments, as shown in FIGS. 18-19, the main body 202 of the orthopedic wedge 200 can be configured to be implanted within a substantially straight osteotomy, such as osteotomy 122, as described above. In such embodiments, the main body 202 can have a substantially straight configuration wherein the overall shape of the main body 202 is not curved in the x-y plane. In some embodiments, the first and/or the second surfaces 208, 210 can have a curved or dished configuration, as described above, or may be planar, depending upon the particular application.

In other embodiments, the orthopedic wedge 200 can be a curved wedge comprising a main body 202 having an overall curved configuration. As shown in FIG. 21, the main body 202 of the wedge can have a first axis extending along the length dimension (e.g., the x-axis), a second axis extending along the width dimension (e.g., the y-axis), and a third axis extending along the thickness dimension (e.g., the z-axis). The main body of the wedge can be curved in a plane 293 defined by the first and third axis (e.g., the x-z plane). The other elements of the orthopedic wedge 200 may be as described above. The first and/or the second surface 208, 210 may also comprise a dished configuration, as described above.

In embodiments wherein the orthopedic wedge is a curved wedge, as shown in FIGS. 20-21, the main body 202 of the orthopedic wedge 200 can be configured to be implanted within a radially curved osteotomy, such as curved osteotomy 124 shown in FIG. 20. In certain embodiments, the curved osteotomy 124 can be a curved cut located distal to the native insertion sites of the caudal cruciate ligament and the medial collateral ligament. The pivot point 126 created by the curved osteotomy 124 can be forward of (e.g., cranial to) the native insertion sites of the caudal cruciate ligament and the medial collateral ligament. This location can mitigate the risk of soft tissue damage such as, for example, cutting the caudal cruciate and/or the medial collateral ligaments. Furthermore, in certain applications the osteotomy location can mitigate surgical trauma to the patient, thus minimizing recovery time, because the joint capsule does not need to be incised. In some embodiments, the curved wedge can comprise a fixation member 260, as described above.

The radially curved osteotomy 124 can be formed as described above using a radial saw blade, or a curved saw guide in lieu of the straight saw guide 500 to align the saw blade for performance of the osteotomy. In some embodiments, the curved osteotomy 124 extends partially but not completely through the tibia, thereby creating a bone portion or "bridge" located, for example, between the tibial tuberosity 109 and the medial and lateral condyles (lateral condyle 111 is visible in FIGS. 18 and 20). The osteotomy 124 can thereby define a pivot point 126 about which the portion 110 of the tibia 104 can pivot to expand the osteotomy 124 and rotate the tibial plateau 108 cranially. In other embodiments, the portion 110 of the tibia 104 containing the tibial plateau 108 can be fully excised from the tibia 104. In such embodiments, the surgeon may not need to use an expander during the implantation procedure.

FIGS. 24-27 illustrate another embodiment of the orthopedic wedge 200 where, in lieu of or in addition to the anchor openings 226, the orthopedic wedge comprises an angled fixation member 278 for anchoring the orthopedic wedge within an osteotomy (e.g., osteotomy 122). The other elements of the orthopedic wedge 200 can be configured according to any of the embodiments described above. The first and second surfaces 208, 210 (see e.g., FIG. 25) of the orthopedic wedge 200 can have a concave or dished configuration, as described above.

Figure 25:
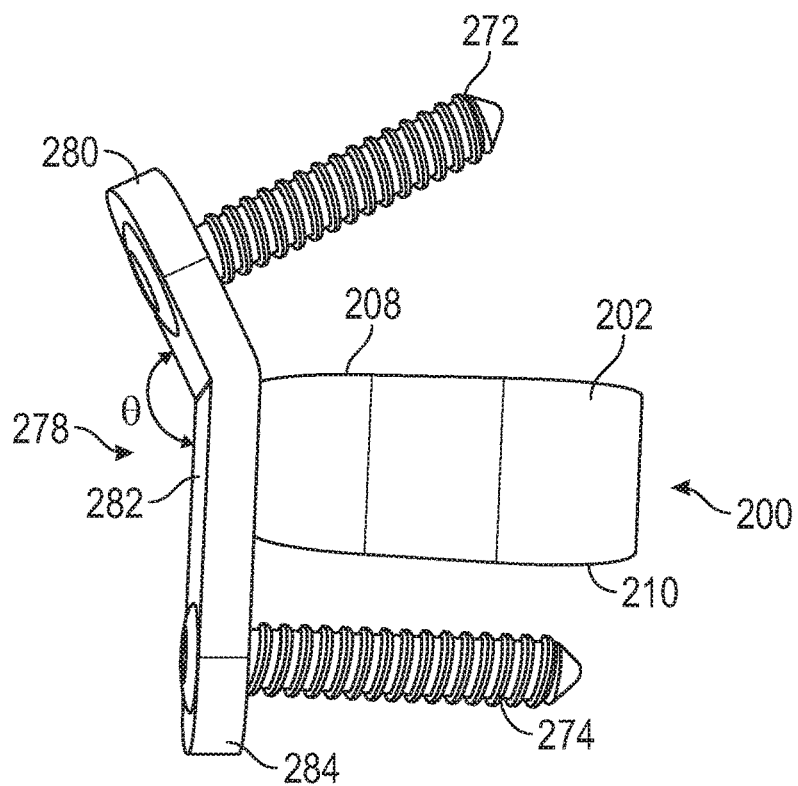
FIG. 25 illustrates an end view of the orthopedic wedge of FIG. 24 including anchoring elements inserted through the fixation member.

The fixation member 278 can comprise a first end portion 280, a center portion 282, and a second end portion 284. The first and second end portions 280, 284 can extend beyond the thickness of the orthopedic wedge. As shown in FIG. 25, the fixation member 278 can be positioned such that the second end portion 284 and the center portion 282 are parallel to the side surface 262 of the main body 202 of the orthopedic wedge. The first end portion 280 can be angled relative to the body 202 of the orthopedic wedge such that the first end portion 284 and the center portion 282 define an angle θ between them. In some embodiments, the angle θ can be from 90° to 180°, 110° to 170°, 120° to 160°, etc. The angled configuration of the first end portion 280 can allow the first end portion to contact or lay flush against the outer surface of the native tibia. For example, as shown in FIG. 27, the first end portion 280 can be angled such that it lays flush against a medial surface 128 of the tibia 104.

The first and second end portions 280, 284 of the fixation member 278 can have first and second apertures 286, 288, respectively. The apertures 286, 288 can extend through the thickness of each respective end portion 280, 284. As shown in FIG. 25, each aperture 286, 288 can be configured to receive a respective anchoring element, such as first and second screws 272, 274. In the illustrated embodiment, the apertures extend straight through the thickness of the fixation member 278. In other embodiments, the apertures 286, 288 can extend at respective angles through the thickness of each respective end portion 280, 284.

Figure 26:
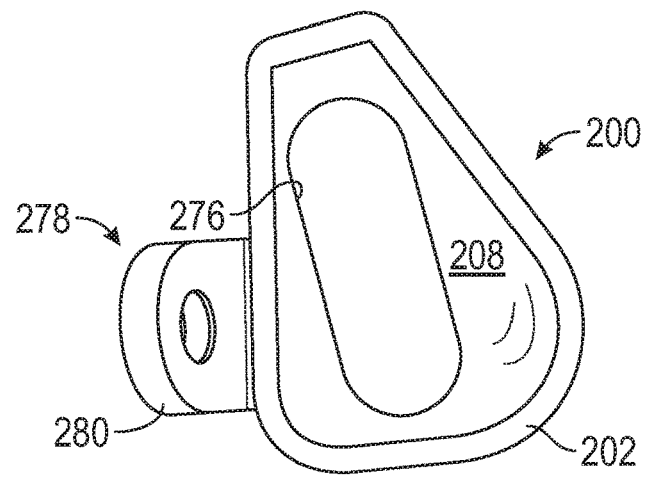
FIG. 26 illustrates a top plan view of the orthopedic wedge of FIG. 24.

In some embodiments, as shown in FIG. 26, the orthopedic wedge 200 can comprise a central slot 276 extending through the main body 202 of the wedge. The central slot 276 can, for example, be configured to accommodate one or more anchoring elements extending through the wedge 200 and/or to promote native bone growth through the wedge 200. For example, in some embodiments, the central slot 276 can comprise biologics within them, for example, bioglass, bone morphogenetic protein (BMP), bone graft materials (e.g., autograft or allograft bone), bone graft substitute materials (ceramics, bone growth factors, etc.), and/or sclerostin.

Figure 27:
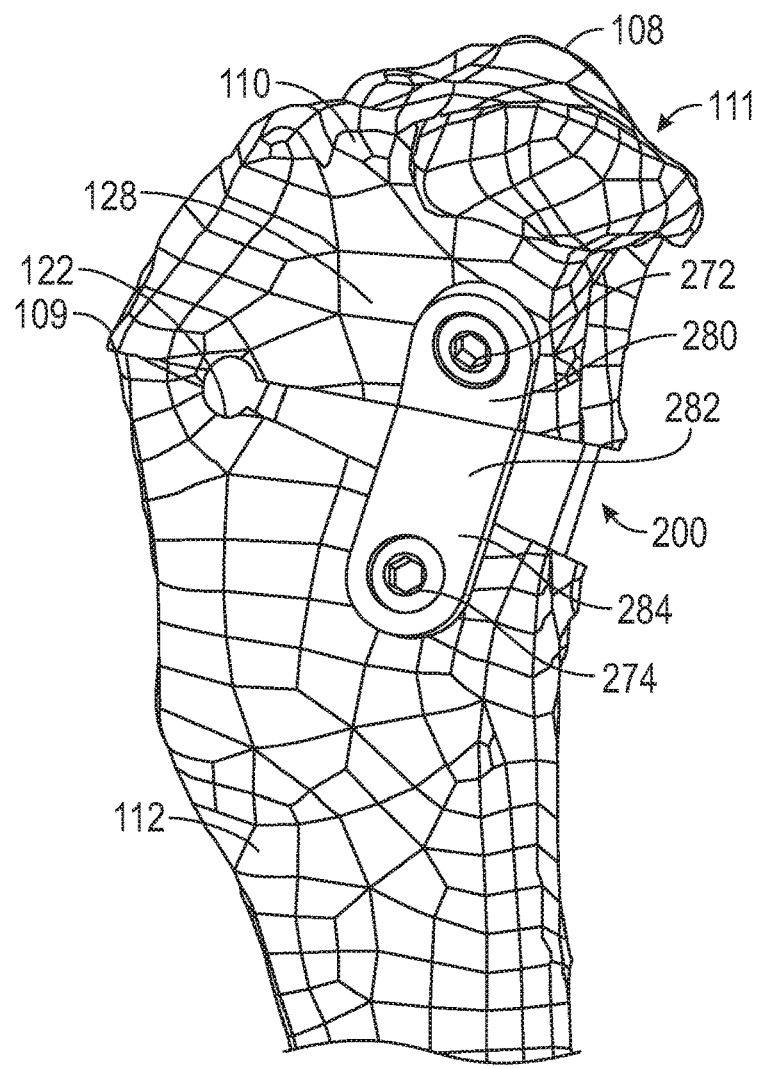
FIG. 27 illustrates a lateral side elevational view of the orthopedic wedge of FIG. 24 implanted within a tibia.

Referring now to FIG. 27, the orthopedic wedge 200 can be implanted within an osteotomy (e.g., osteotomy 122) similar to the osteotomies described above. For example, the first screw 272 can extend through the first aperture 286 and into a proximal portion 110 of the tibia, and a second screw 274 can extend through the second aperture 288 and into a portion 112 of the tibia distal to the osteotomy, anchoring the wedge 200 to the bone. In other embodiments, the first screw 272 can extend through the first aperture 286, through the central slot 276 of the wedge, and into the portion 112 of the tibia. The second screw 274 can extend through the second aperture 288, through the central slot 276, and into the portion 110 of the tibia. This configuration allows the wedge to be tightened against the bone in both directions, improving initial stability, and compressing the wedge against the bone.

Figure 28:
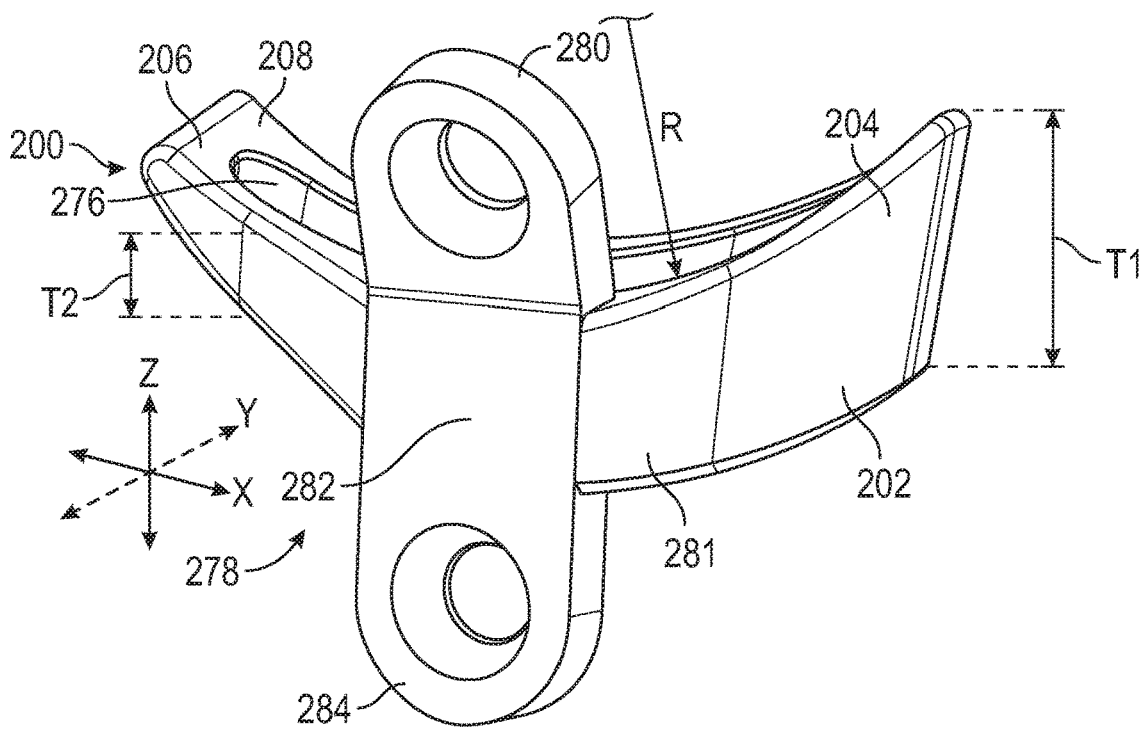
FIG. 28 illustrates a perspective view of another embodiment of an orthopedic wedge.
Figure 29:
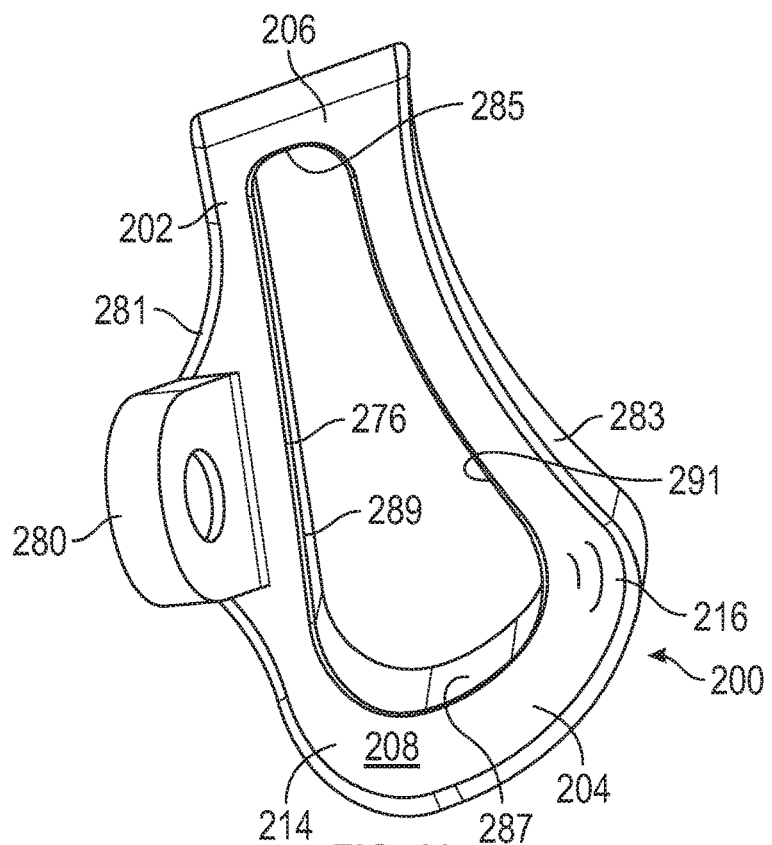
FIG. 29 illustrates a top plan view of the orthopedic wedge of FIG. 28.
Figure 30:
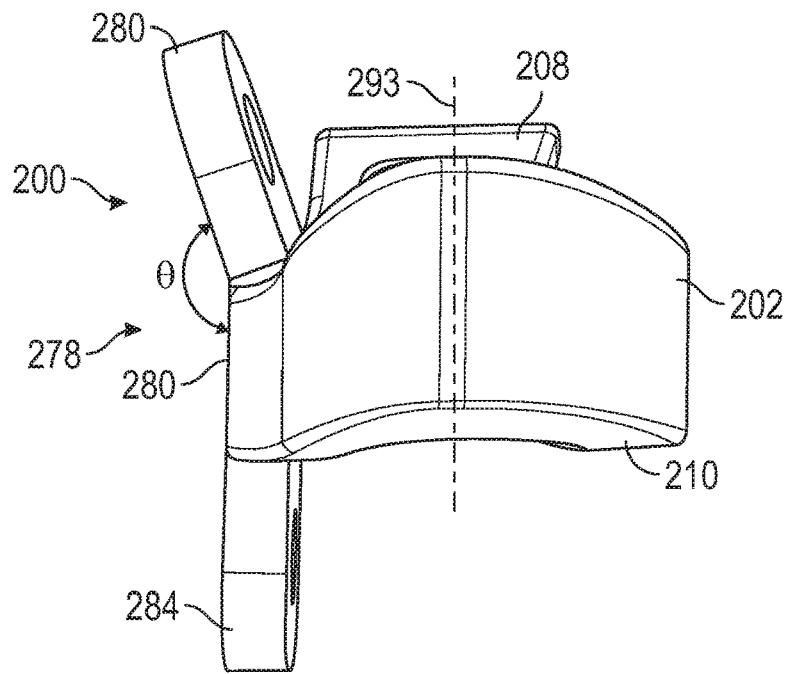
FIG. 30 illustrates an end view of the orthopedic wedge of FIG. 28.

FIGS. 28-31 illustrate another embodiment of the orthopedic wedge 200 where, in lieu of or in addition to the anchor openings 226, the orthopedic wedge comprises an angled fixation member 278 for anchoring the orthopedic wedge within an osteotomy (e.g., radially curved osteotomy 124), and where the orthopedic wedge is a curved wedge comprising a main body 202 having an overall curved configuration. As shown in FIG. 28, the main body 202 of the wedge can have a first axis extending along the length dimension (e.g., the x-axis), a second axis extending along the width dimension (e.g., the y-axis), and a third axis extending along the thickness dimension (e.g., the z-axis). Referring now to FIG. 30, the main body of the wedge can be curved in a plane 293 defined by the first and third axis (e.g., the x-z plane). The curvature of the body 202 can be defined by a circle having a radius R. The other elements of the orthopedic wedge 200 can be configured according to any of the embodiments described above. The first and/or the second surface 208, 210 may also comprise a concave or dished configuration, as described above. The orthopedic wedge 200 can also comprise an angled fixation member 278, as described above.

As shown in FIG. 28, the wedge 200 has a base portion 204 and an apical portion 206. The thickness of the wedge can taper from the base portion to the apical portion. That is, the base portion 204 can have a first thickness $T_1$ measured along the z-axis at the thickest portion of the base, and the apical portion 206 can have a second thickness $T_2$ at the apical portion 206. In some embodiments, the first thickness $T_1$ can be greater than the second thickness $T_2$.

Referring now to FIG. 29, The base portion 204 can comprise first and second lobe portions 214, 216 having radii similar to those shown in FIG. 6C above. In some embodiments, the radius of the first lobe can be greater than the radius of the second lobe, such that the outer profile geometry of the orthopedic wedge 200 resembles a cross-section of the canine tibia. The wedge 200 can comprise a first edge 281 and a second edge 283 extending from the base portion 204 and angled relative to (e.g., generally toward) each other. The first edge 281 can have a convex shape, and the second edge 283 can have a curved shape that mimics the curved lateral surface 119 (see e.g., FIG. 6B) of the native tibia 104.

In some embodiments, the wedge 200 can comprise a central slot 276 extending through the thickness of the body 202. The slot 276 can have an apical portion 285 and a base portion 287 situated adjacent to the apical and base portions 206, 204 of the main body 202. The base portion 287 of the slot can have a curved shape comprising two lobe portions that correspond respectively with first and second lobe portions 214, 216. The apical portion 285 of the slot can have a curved shape with respect to the apical portion 206 of the wedge. The slot can comprise a first edge 289 and a second edge 291 extending from the base portion 287 and angled relative to (e.g., toward) each other. The first edge 289 can be substantially straight until it intersects the first lobe, and the second edge 291 can have a curved shape that mimics the curved surface of the second edge 283.

In some embodiments, the center portion 282 of the angled fixation member 278 can be formed integrally with the main body of the wedge 202, such that the first and second end portions 280, 284 of the angled fixation member extend from the first and second surfaces 208, 210 of the orthopedic wedge, respectively. In such embodiments, the thickness of the center portion 282 can be encompassed by or within the perimeter of the wedge.

Figure 31:
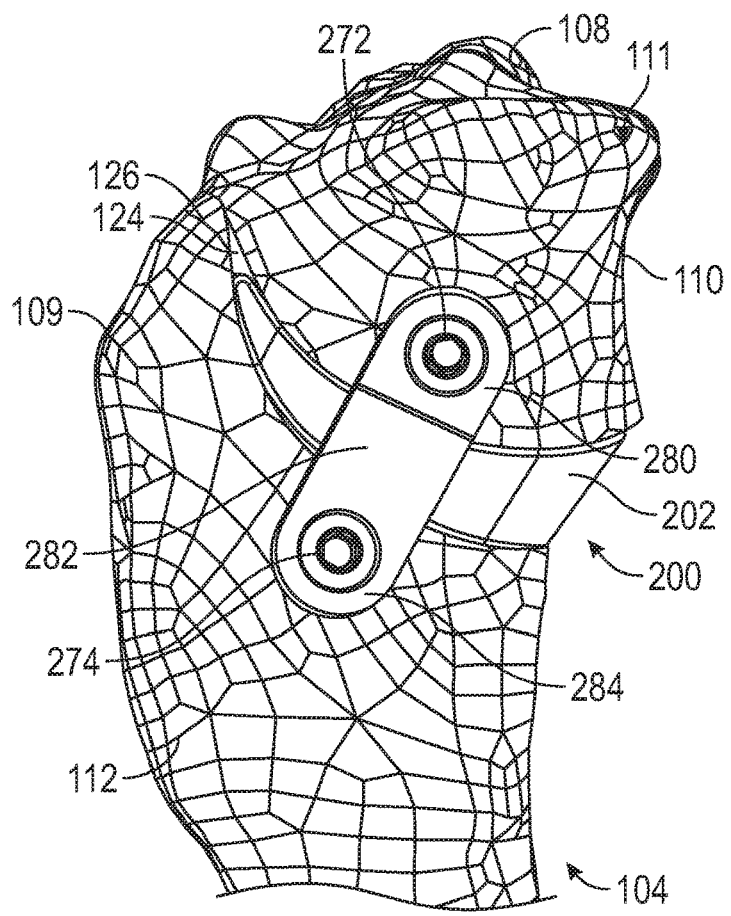
FIG. 31 illustrates a lateral side elevational view of the orthopedic wedge of FIG. 28 implanted within a tibia.
Figure 32:
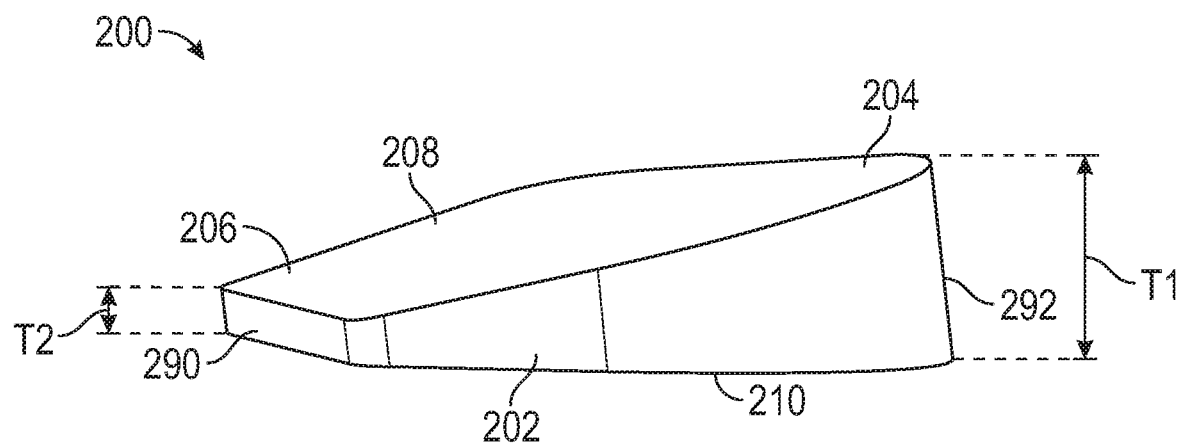
FIG. 32 illustrates a perspective view of another embodiment of an orthopedic wedge.

As described above, the curved wedge 200 can be implanted within a radially curved osteotomy 124, as shown in FIG. 31. The first end portion 280 of the angled fixation member 278 can be angled such that it lays flush against, for example, a medial surface of the tibia 104.

FIGS. 32-36 illustrate another embodiment of the prosthetic wedge 200 which can be implanted in conjunction with one or more fixation elements such as surgical staples, as described in more detail below. The prosthetic wedge 200 can have a main body 202 comprising a first end configured as a base portion 204 and a second end configured as an apical portion 206. The thickness of the wedge can taper from a first thickness $t_1$ at the base portion 204 to a second thickness $t_2$ that is less than $t_1$, similar to the embodiments described above.

Figure 33:
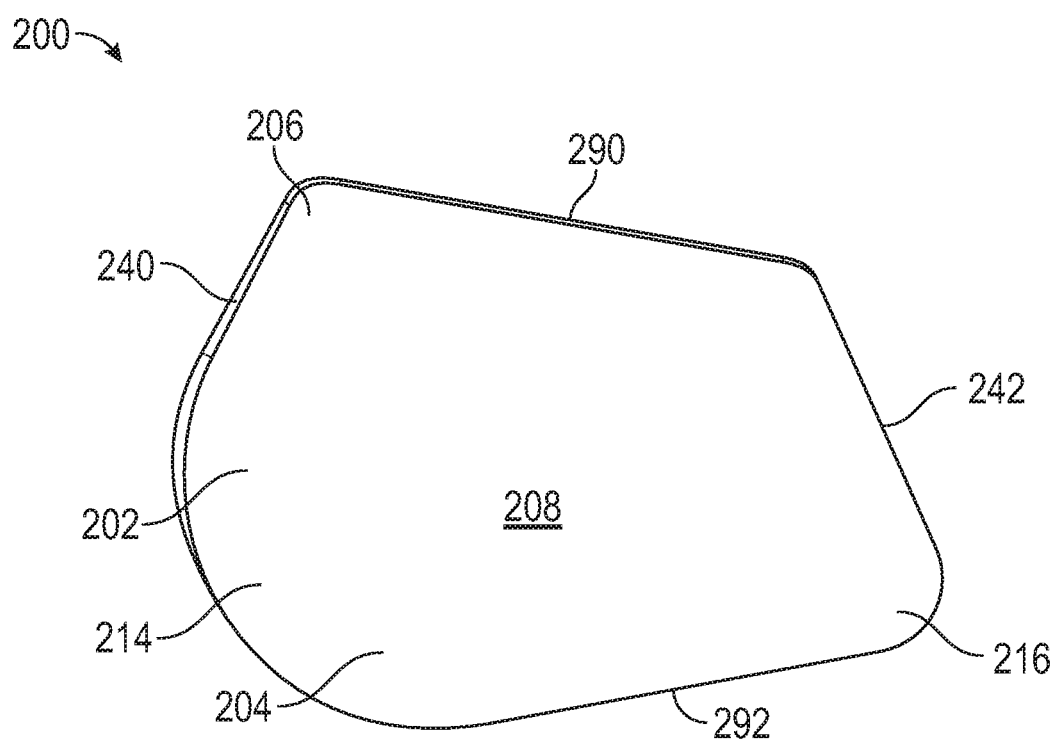
FIG. 33 illustrates a top plan view of the orthopedic wedge of FIG. 32.

Referring now to FIG. 33, the base portion can comprise curved portions or lobes 214 and 216 having radii similar to those shown in FIG. 6C above. The wedge 200 can comprise a first edge 240 and a second edge 242 extending from the base portion 204 and angled relative to (e.g., toward) each other. The first edge 240 can have a convex shape or a straight shape, and the second edge 242 can have a substantially straight shape until it intersects the second lobe portion 216. In addition to first and second edges 240 and 242, the wedge 200 can have a third edge 290 located at the apical portion 206 of the main body 202 and a fourth edge 292 located at the base portion 204. The third and fourth edges 290, 292 can be angled relative to (e.g., toward) each other in, for example, the lateral direction when implanted.

Figure 34:
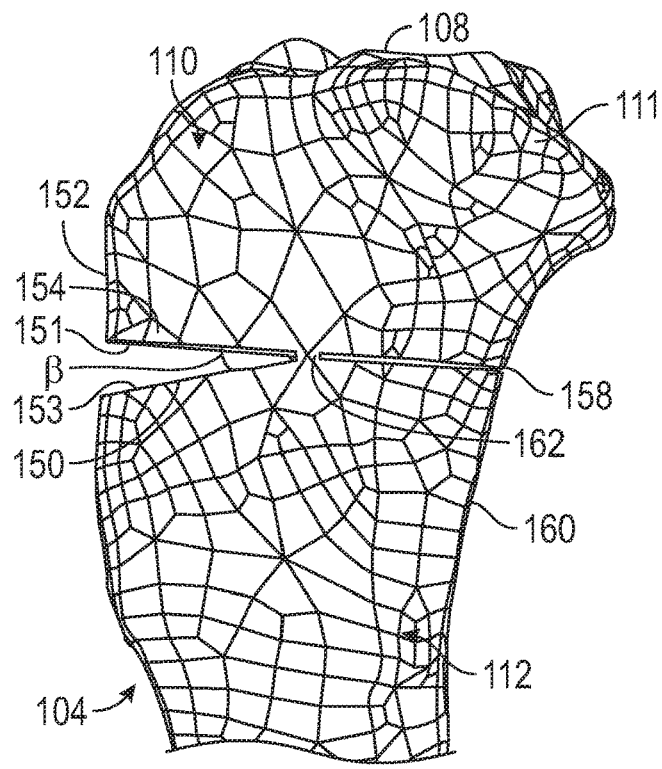
FIG. 34 illustrates a lateral side elevational view of a tibia including multiple osteotomies formed in preparation for insertion of the wedge of FIG. 32.
Figure 35:
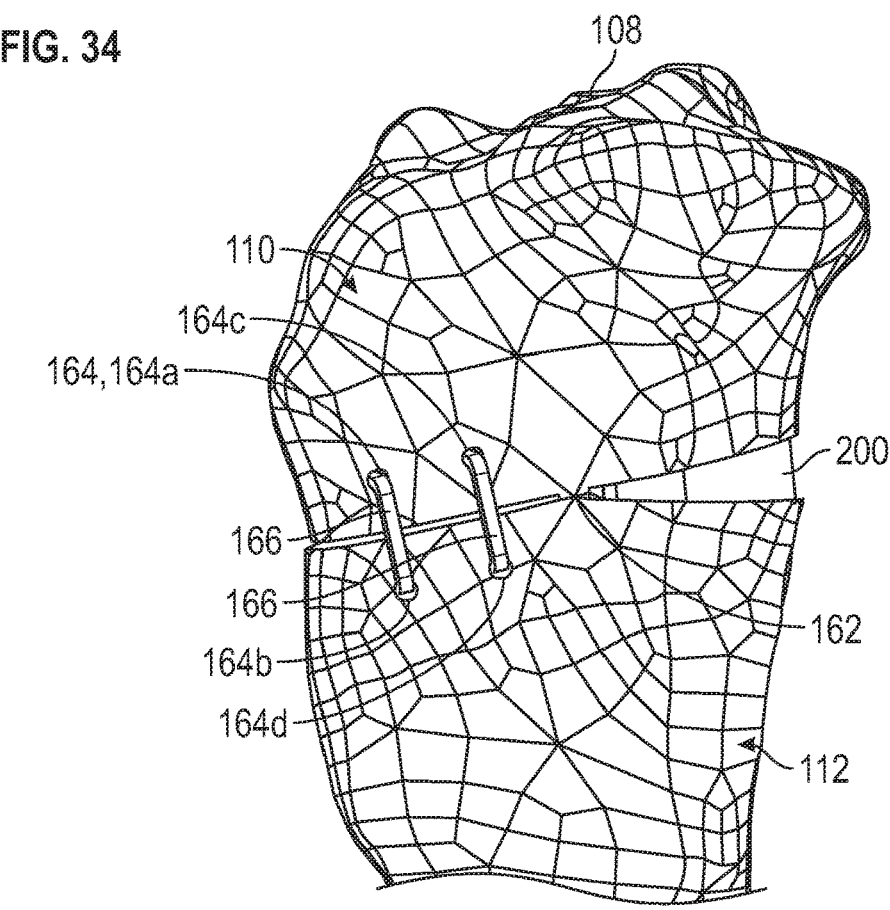
FIG. 35 illustrates a lateral side elevational view of the orthopedic wedge of FIG. 32 implanted within the caudal osteotomy in the tibia.
Figure 36:
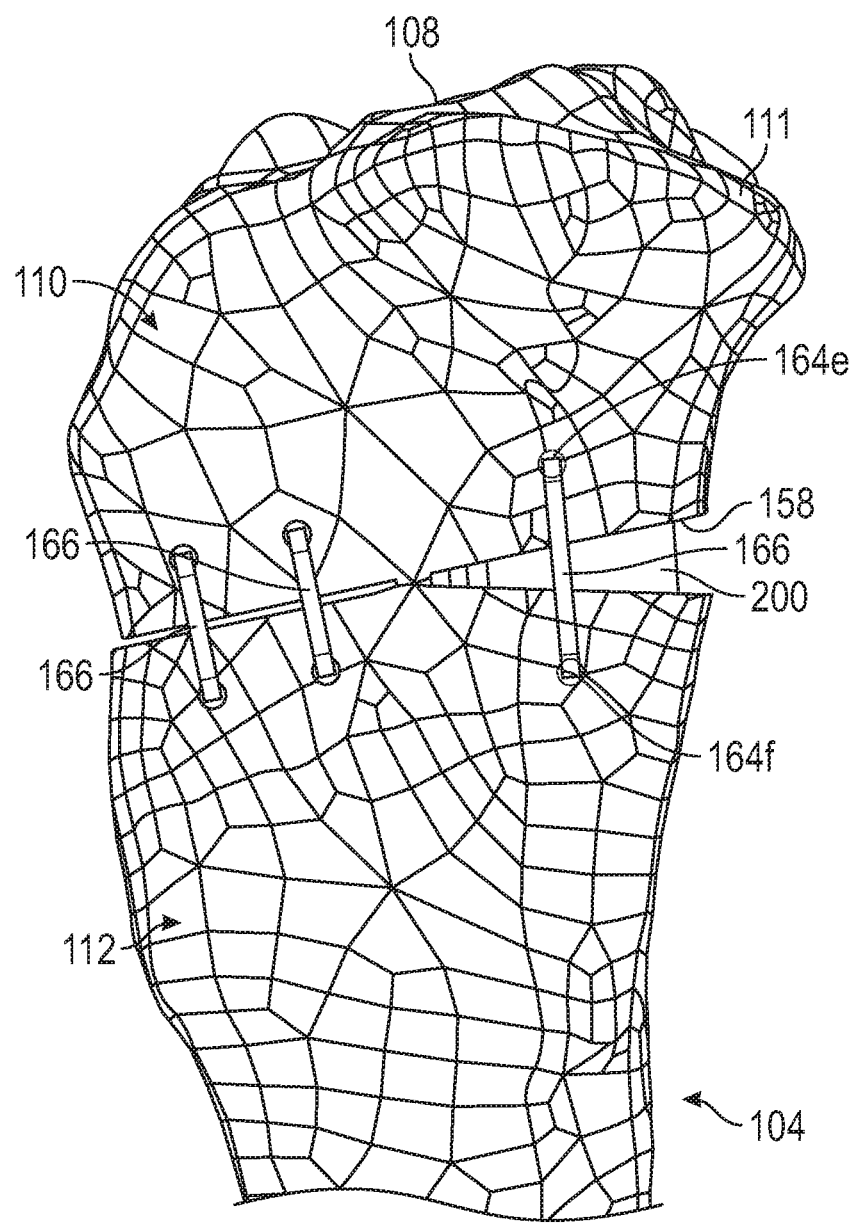
FIG. 36 illustrates a lateral side elevational view of the orthopedic wedge of FIG. 32 implanted within a tibia.

As shown in FIGS. 34-36, the orthopedic wedge 200 can be implanted within a tibia 104 to adjust the angle of the tibial plateau 108 using the following exemplary method. This method can be used with any of the above-described embodiments, but, for ease of reference, will be described with reference to the embodiment shown in FIGS. 32-33.

Referring now to FIG. 34 a surgeon can cut (e.g., using a saw guide such as saw guide 300 or 500 described above) a first osteotomy 150. The cut can be made in the cranial surface 152 of the tibia 104, can extend in a cranial-caudal direction, and can be angled proximally toward the lateral condyle 111. In some embodiments, the first osteotomy 150 can extend less than mid-way through the thickness of the tibia. The surgeon can then cut a second osteotomy 154 proximal to the first osteotomy 150. The second osteotomy 154 can be made in the cranial surface 152 of the tibia and can extend in the cranial-caudal direction. The first and second osteotomies can intersect, defining an angle β between them. In some embodiments, the angle β can be from 5° to 60°, 5° to 45°, 10° to 30°, etc. The surgeon can remove a bone wedge from between the two osteotomies 150, 154, creating a void or gap in the tibia 104 defined by first and second surfaces 151, 153.

The surgeon can then cut a third osteotomy 158 in the caudal surface 160 of the tibia extending in the cranial-caudal direction. The third osteotomy can be aligned with (e.g., parallel to) the second osteotomy 154 and can extend less than midway through the thickness of the tibia, such that the second and third osteotomies 154, 158 define a bone portion or "bridge" 162 between them.

In other embodiments, in lieu of third osteotomy 158, the second osteotomy 154 can extend fully through the tibia 104 in the cranial-caudal direction, fully excising the proximal tibial portion 110 of the tibia containing the tibial plateau 108. In such embodiments, the surgeon need not use an expander during the implantation procedure and may reposition the portion 110 of the tibia as needed to adjust the angle of the tibial plateau.

Referring now to FIG. 35, the third osteotomy 158 (FIG. 34) can be expanded using the expansion apparatus and methods described above, and the orthopedic wedge 200 can be implanted therein. The insertion of the orthopedic wedge 200 can cause the proximal portion 110 of the tibia 104 to pivot around the bone portion 162 such that the tibial plateau 108 is rotated cranially. The rotation of the tibia portion 110 causes the first surface 151 to pivot toward second surface 153, thus reducing the gap in the cranial aspect of the tibia formed by the extraction of the bone wedge. The surgeon can drill a plurality of openings 164 above (e.g. proximal to) and/or below (e.g., distal to) the first and second osteotomies 150, 154. The openings can extend through the tibia 104 in a medial-lateral direction.

One or more fixation elements 166 (e.g., surgical staples) can be inserted in the one or more apertures 164. The fixation elements 166 can mitigate movement of the proximal portion 110 of the tibia and can improve initial stability.

In some embodiments, as shown in FIG. 35, the tibia includes four apertures 164, oriented as opposing pairs 164a, 164b and 164c, 164d, wherein one aperture of each pair is located proximal to the first and second osteotomies and the other aperture of each pair is located distal to the first and second osteotomies. A respective fixation element 166 can be inserted in opposing pairs of apertures (e.g., apertures 164a, 164b).

Referring now to FIG. 36, in some embodiments, the tibia can include two additional apertures 164 oriented as an opposing pair 164e, 164f. One aperture (e.g., aperture 164e) can be located proximal to the third osteotomy 158, and the other aperture (e.g., aperture 164f) can be located distal to the third osteotomy 158. An additional fixation element 166 can be coupled to the apertures 164e, 164f. The additional fixation element can mitigate movement of the wedge 200 within the third osteotomy 158, can improve initial stability, and can compress the wedge against the bone.

Any of the above described orthopedic wedges can be formed from bioresorbable materials such that after implantation of the orthopedic wedge within an osteotomy, the orthopedic wedge resorbs or dissolves over a selected period of time (e.g., over 3-4 months post-implantation) and is absorbed by the patient's body. The gradual dissolution of the orthopedic wedge can allow for natural bone regrowth within the osteotomy.

In a representative embodiment, a bioresorbable orthopedic wedge having a bioresorbable fixation member can be used in the following exemplary manner. A cranial-caudal osteotomy can be cut in a patient's tibia using the method described above. The osteotomy can then be expanded such that the bioresorbable wedge can be inserted therein. The wedge can then be anchored to the bone using a first porous biocompatible anchoring element extending through the first opening in the fixation member, through the wedge, and into the distal portion of the tibia, and a second porous biocompatible anchoring element extending through the second opening in the fixation member, through the wedge, and into the proximal portion of the tibia. The wedge can be tightened against the bone in both directions, compressing the wedge against the bone. Over time the bioresorbable wedge will dissolve and be absorbed by the patient's body simultaneously with the growth of natural bone within the osteotomy, filling the space vacated by the wedge. Once the wedge and the fixation member are fully absorbed, only the first and second anchoring elements remain. A surgeon can perform a stab incision to remove the first and second anchoring elements from the tibia.

While the illustrated embodiment describes implantation of the orthopedic wedge within the tibia of a patient, the orthopedic wedge can be implanted in any of various bones, such as, without limitation, the femur, the radius, the ulna, the fibula, etc. The wedge embodiments described herein may also be used in any of a variety of species, including canids, felines, primates including humans and non-human primates, equids, camelids, etc.

Example 1

Figure 16B:
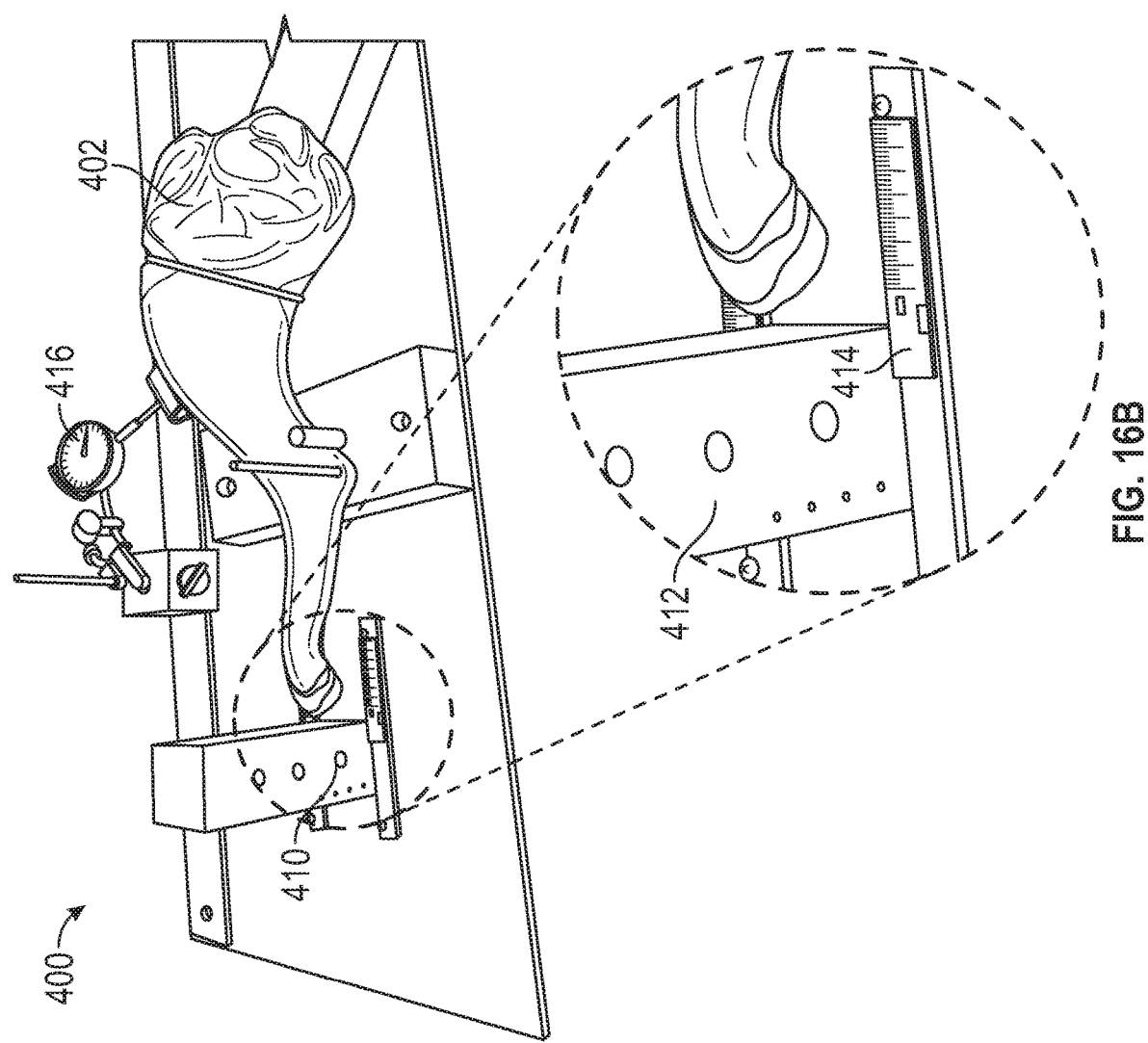
FIGS. 16A and 16B illustrate an experimental set-up for testing the functionality of an embodiment of an implantable orthopedic wedge.
Figure 16A:
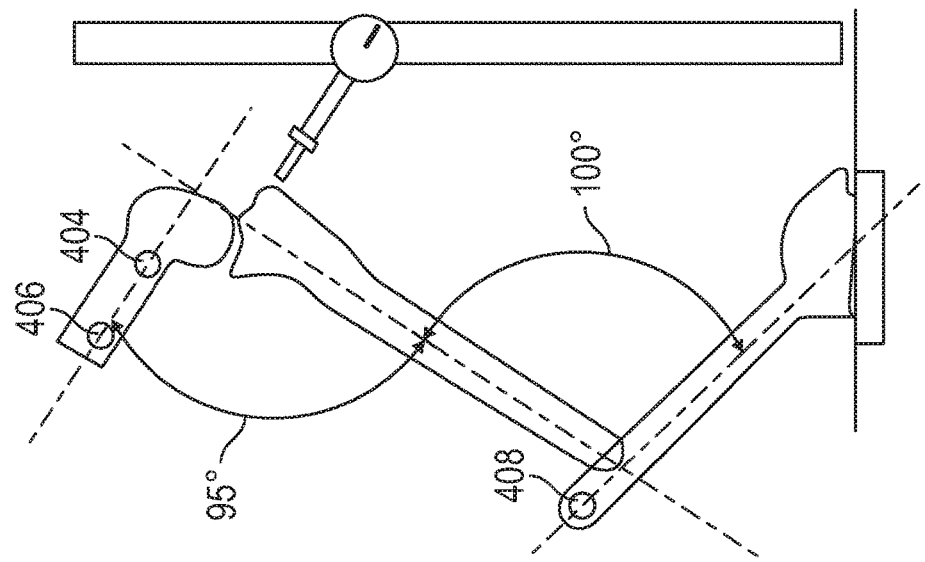
Figure 17:
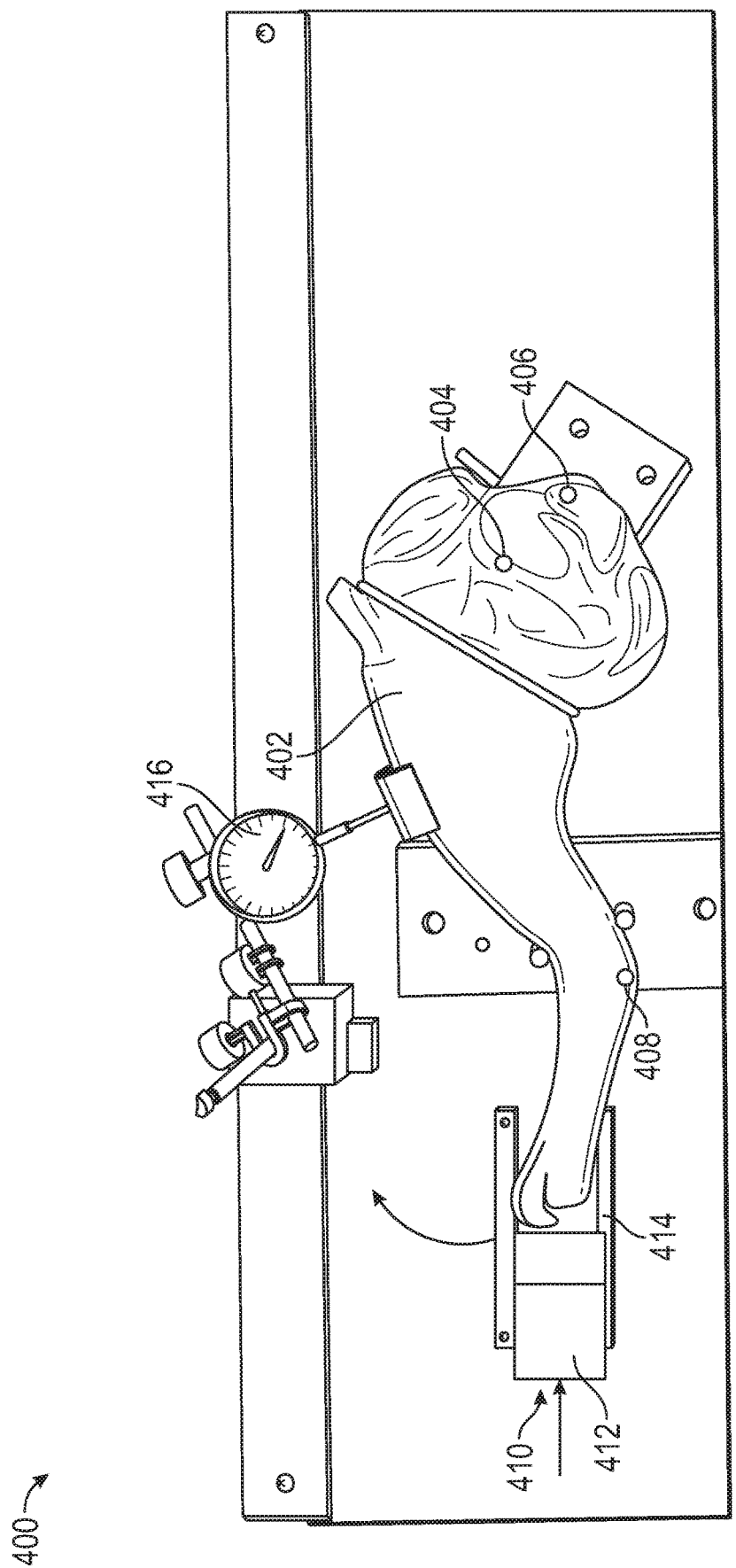
FIG. 17 illustrates a top plan view of the experimental set-up of FIGS. 16A and 16B.

The following is an example in which an implantable orthopedic wedge as described above was implanted in a tibia of a canine cadaver hindlimb. FIGS. 16A, 16B, and 17 illustrate the experimental set-up as described herein.

Methods.

In this example, a tibial compression test was used to assess the functionality of the orthopedic wedge osteotomy procedure to address a torn cranial cruciate ligament. A tibial compression test is typically used to determine whether the cranial cruciate ligament has been damaged or torn. If the cranial cruciate ligament (CrCL) is torn, the tibial tuberosity will move cranially when the femur is held as the hock (e.g., the ankle) is flexed. Flexion of the hock causes tension in the gastrocnemius muscle, which in turn displaces the tibia cranially as the CrCL is unable to resist the thrust. When the exam is performed on a patient having a torn CrCL, the tibia advances cranially to an observable degree.

Testing.

As shown in FIG. 12, an experimental fixture 400 was used to hold a canine cadaver hindlimb and provide the ability to monitor tubercle advancement during flexion of the hock. The experimental protocol included first measuring the tubercle advancement of a canine cadaver hindlimb having an intact CrCL, measuring the tubercle advancement again after having severed the CrCL, and then measuring the tubercle advancement post implantation of various orthopedic wedges in order to evaluate the restoration of knee stability.

Referring still to FIG. 12, a right cadaver limb 402 was mounted to the experimental fixture 400 in the following manner. First a 4 mm drill was placed through the femoral head and into the experimental fixture to create a first fixation point 404, then a 2.5 mm opening was drilled through the mid-shaft of the femur and into the experimental fixture to create a second fixation point 406, and finally a 4 mm drill was placed through the calcaneus into the experimental fixture to create a third fixation point 408.

A slide assembly 410 was used to flex the hock. The slide assembly 410 comprised a block 412 and a measurement device 414. The block was used to flex the hock, and the measurement device was used to determine the amount of flexion applied. A dial indicator 416 was applied to the knee (e.g., the stifle) of the cadaver to measure the advancement of the tibial tubercle. For each tested tibial plateau position, the hock was flexed by advancing the block 412 of the slide assembly 410 by 35 mm.

The tibial plateau positions tested were: (1) limb intact, (2) partial cut of the patellar ligament and a complete cut of the medial collateral ligament, (3) complete cut of the cranial cruciate ligament, (4) orthopedic wedge #4 implanted, having a wedge angle of 13 degrees and a maximum thickness $T_1$ of 6 mm, (5) orthopedic wedge #7 implanted, having a wedge angle of 18 degrees and a maximum thickness $T_1$ of 8 mm. The orthopedic wedges were implanted in the manner described above. The results are presented below in Table 1.

TABLE 1

| Test No. | Position | Tibial Cranial Movement |
| --- | --- | --- |
| 1 | Cadaver limb intact | 0.075 inches |
|  | Repeat of (1) | 0.067 inches |
|  | Repeat of (1) | 0.067 inches |
| 2 | Incision to bone | 0.090 inches |
|  | Repeat of (2) | 0.088 inches |
| 3 | Cranial Cruciate Ligament cut | 0.150 inches |
|  | Repeat of (3) | 0.160 inches |
| 4 | #4 Device Implanted | 0.110 inches |
|  | Repeat of (4) | 0.105 inches |
| 5 | #7 Device Implanted | 0.075 inches |
|  | Repeat of (5) | 0.077 inches |

CONCLUSIONS

The tibial plateau was able to be corrected from an angle of 25 degrees to an angle of 7 degrees using an 18 degree orthopedic wedge (#7 device).

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

What is claimed is:

1. A tibial implantable orthopedic wedge configured to be implanted within an osteotomy in a tibia, the orthopedic wedge comprising:
   a main body having a base portion and an apical portion, the base portion comprising at least one lobe; and
   a substantially cylindrical positioning member coupled to the apical portion;
   wherein a thickness of the main body tapers from a first thickness at the base portion to a second thickness at the apical portion, the first thickness being greater than the second thickness, and
   wherein a width of the main body tapers from a first width at the base portion to a second width at the apical portion, the first width being greater than the second width,
   wherein the main body comprises first and second surfaces and wherein the first and second surfaces are concave such that peripheral edge portions of the first and second surfaces extend beyond center portions of the first and second surfaces,
   wherein the positioning member extends in a medial-lateral direction and has a thickness greater than the second thickness of the main body,
   wherein:
      the at least one lobe is a first lobe;
      the base portion further comprises a second lobe on an opposite side of the base portion from the first lobe;
      the first lobe comprises a first radius and a curved edge configured to align with a cross-section of a medial condyle of a tibia;
      the second lobe comprises a second radius and a curved edge configured to align with a cross-section of a lateral condyle of the tibia; and
      the first radius is different from the second radius.

2. The implantable orthopedic wedge of claim 1, further comprising one or more openings extending through the thickness of the main body.

3. The implantable orthopedic wedge of claim 2, wherein at least one of the one or more openings is configured to receive an anchoring element to anchor the wedge to an implantation site.

4. The implantable orthopedic wedge of claim 1, wherein the wedge comprises a bioresorbable material.

5. The implantable orthopedic wedge of claim 4, wherein the bioresorbable material is selected from the group consisting of poly-L-lactic acid (PLLA), polyglycolic acid (PGA), and hydroxyapatite PLLA (HA/PLLA).

6. The implantable orthopedic wedge of claim 1, further comprising a fixation member configured to receive one or more anchoring elements to anchor the wedge to an implantation site.

7. The implantable orthopedic wedge of claim 6, wherein the fixation member is coupled to a side surface of the main body and extends parallel to the thickness of the main body.

8. The implantable orthopedic wedge of claim 6, wherein the fixation member has a first end portion and a second end portion each comprising a respective aperture, and wherein each aperture is configured to receive a respective anchoring element of the one or more anchoring elements.

9. The implantable orthopedic wedge of claim 8, the main body comprising a central slot extending through the thickness of the main body, the central slot configured to allow the one or more anchoring elements to extend through the central slot.

10. The implantable orthopedic wedge of claim 1, the wedge having a first axis extending along a length dimension, a second axis extending along a width dimension, and a third axis extending along a thickness dimension, wherein the main body of the wedge is curved in a plane defined by the first and third axes.

* * * * *